United States Patent
Anderson et al.

(10) Patent No.: US 7,371,067 B2
(45) Date of Patent: May 13, 2008

(54) SIMULATION METHOD FOR DESIGNING CUSTOMIZED MEDICAL DEVICES

(75) Inventors: James H. Anderson, Columbia, MD (US); William R. Brody, Baltimore, MD (US); Chee-Kong Chui, Singapore (SG); Yiyu Cai, Singapore (SG); Yaoping Wang, Singapore (SG); Wieslaw L. Nowinski, Singapore (SG)

(73) Assignees: The Johns Hopkins University School of Medicine, Baltimore, MD (US); **Agency for Science, Technology & Research (A*Star)**, Singapore (SG)

( * ) Notice: Subject to any disclaimer, the term of this patent is extended or adjusted under 35 U.S.C. 154(b) by 401 days.

(21) Appl. No.: 10/091,745

(22) Filed: Mar. 5, 2002

(65) Prior Publication Data

US 2002/0137014 A1 Sep. 26, 2002

Related U.S. Application Data

(60) Provisional application No. 60/273,734, filed on Mar. 6, 2001, provisional application No. 60/273,733, filed on Mar. 6, 2001.

(51) Int. Cl.
*G09B 23/28* (2006.01)
(52) U.S. Cl. .................. 434/262; 623/901; 700/95; 700/96; 700/97; 700/98; 703/13
(58) Field of Classification Search .............. 434/262, 434/267; 703/1, 6, 7; 345/964, 970; 382/130–132; 600/101, 104, 129; 128/920, 922; 623/99; 700/95
See application file for complete search history.

(56) References Cited

U.S. PATENT DOCUMENTS

| | | | | |
|---|---|---|---|---|
| 4,918,620 A | * | 4/1990 | Ulug | ........................ 706/59 |
| 5,099,846 A | | 3/1992 | Hardy | |

(Continued)

FOREIGN PATENT DOCUMENTS

WO   WO 96/28800   9/1996

(Continued)

OTHER PUBLICATIONS

Cai, Y. Parametrical Modeling Based Multi-Layered Approach for Design and Validation of Catheterization Devices, Jun. 1-4, 1998, Proceedings of the IASTED International Conference, Computer Graphics and Imaging. pp. 32-35.*

(Continued)

*Primary Examiner*—Robert E. Pezzuto
*Assistant Examiner*—Cameron Saadat
(74) *Attorney, Agent, or Firm*—Peter F. Corless; William J. Daley, Jr.; Edwards Angell Palmer & Dodge LLP

(57) ABSTRACT

The invention provides a system for virtually designing a medical device conformed for use with a specific patient. Using the system, a three-dimensional geometric model of a patient-specific body cavity or lumen is reconstructed from scanned volume images such as obtained x-rays, magnetic resonance imaging (MRI), computer tomography (CT), ultrasound (US), angiography or other imaging modalities. Knowledge of the physical properties of the cavity/lumen is obtained by determining the relationship between image density and the stiffness or elasticity of tissues in the body cavity or lumen and is used to model interactions between a simulated device and a simulated body cavity or lumen.

66 Claims, 8 Drawing Sheets

U.S. PATENT DOCUMENTS

| | | | |
|---|---|---|---|
| 5,155,435 A | 10/1992 | Kaufman et al. | 324/309 |
| 5,208,768 A * | 5/1993 | Simoudis | 716/5 |
| 5,297,054 A * | 3/1994 | Kienzle et al. | 700/182 |
| 5,298,115 A * | 3/1994 | Leonard | 216/52 |
| 5,487,012 A * | 1/1996 | Topholm et al. | 700/163 |
| 5,522,402 A | 6/1996 | Cooley | |
| 5,552,995 A * | 9/1996 | Sebastian | 700/97 |
| 5,683,243 A | 11/1997 | Andreiko et al. | |
| 5,704,791 A | 1/1998 | Gillio | 434/262 |
| 5,741,215 A * | 4/1998 | D'Urso | 600/407 |
| 5,754,738 A * | 5/1998 | Saucedo et al. | 706/11 |
| 5,768,134 A * | 6/1998 | Swaelens et al. | 700/121 |
| 5,771,310 A | 6/1998 | Vannah | |
| 5,797,849 A | 8/1998 | Vesely et al. | |
| 5,824,085 A * | 10/1998 | Sahay et al. | 128/898 |
| 5,871,018 A | 2/1999 | Delp et al. | |
| 6,038,488 A | 3/2000 | Barnes et al. | 700/161 |
| 6,106,301 A | 8/2000 | Merril | 434/262 |
| 6,112,109 A * | 8/2000 | D'Urso | 600/407 |
| 6,205,411 B1 * | 3/2001 | DiGioia et al. | 703/11 |
| 6,315,553 B1 | 11/2001 | Sachdeva et al. | |
| 6,327,491 B1 | 12/2001 | Franklin et al. | |
| 6,463,351 B1 * | 10/2002 | Clynch | 700/163 |
| 2001/0047251 A1 * | 11/2001 | Kemp | 703/1 |

FOREIGN PATENT DOCUMENTS

| | | | |
|---|---|---|---|
| WO | WO 98/03954 | | 1/1998 |
| WO | WO 98/10387 | | 3/1998 |
| WO | WO 98/30176 | * | 7/1998 |
| WO | WO 99/16352 | | 4/1999 |
| WO | WO99/39315 | | 8/1999 |

OTHER PUBLICATIONS

CathWorks (A CAD-integrated and Feature-based System for Designing, Presenting and Validating Catheterization Devices) Version 12, Aug. 1999, pp. 1-2.*

James A. Anderson, et al.; *A Vascular Catheterization Simulator for Training and Treatment Planning*; J. Digital Imaging; vol. 11, No. 3; Suppl. 1; 1998; pp. 120-123.

James A. Anderson, et al.; *Virtual Reality in Interventional Radiology*; Min Invas Ther & Allied Technol; 1997; vol. 6; pp. 111-116.

HT Medical Systems, Inc.; Information sheet.

S.B. Issenberg, et al.; *Simulation Technology for Health Care Professional Skills Training and Assessment*; JAMA; vol. 282; No. 9; 1999; pp. 1-18.

Ralf A. Kockro, et al.; *Planning and Simulation of Neurosurgery in a Virtual Reality Environment*; Neuosurgery; vol. 46; No. 1; 2000.

W. Lawton, et al.; *Tubes in Tubes: Catheter Navigation in Blood Vessels and its Applications*; International J. of Solids and Structures; vol. 37; 2000; pp. 3031-3054.

Kent Ridge Digital Labs; *Icard-Real-Time Interactive Simulator for Percutaneous Coronary Revascularization Procedures*; Version 25, 1998; Information Sheet.

Charles A. Taylor, et al.; *Predictive Medicine: Computational Techniques in Therapeutic Decision-Making*; Computer Aided Surgery; 4:231-247; 1999.

Kenneth C. Wang, et al.; *Improving Geometric Model Construction for Blood Flow Modeling*, IEEE Engineering in Medicine and Biology; 1999; pp. 33-39.

Wang et al., Real-Time Interactive Simulator for Percutaneous Coronary Revascularization Procedures, Biomedical Paper, Computer Aided Surgery 3:211-227 (1998).

* cited by examiner

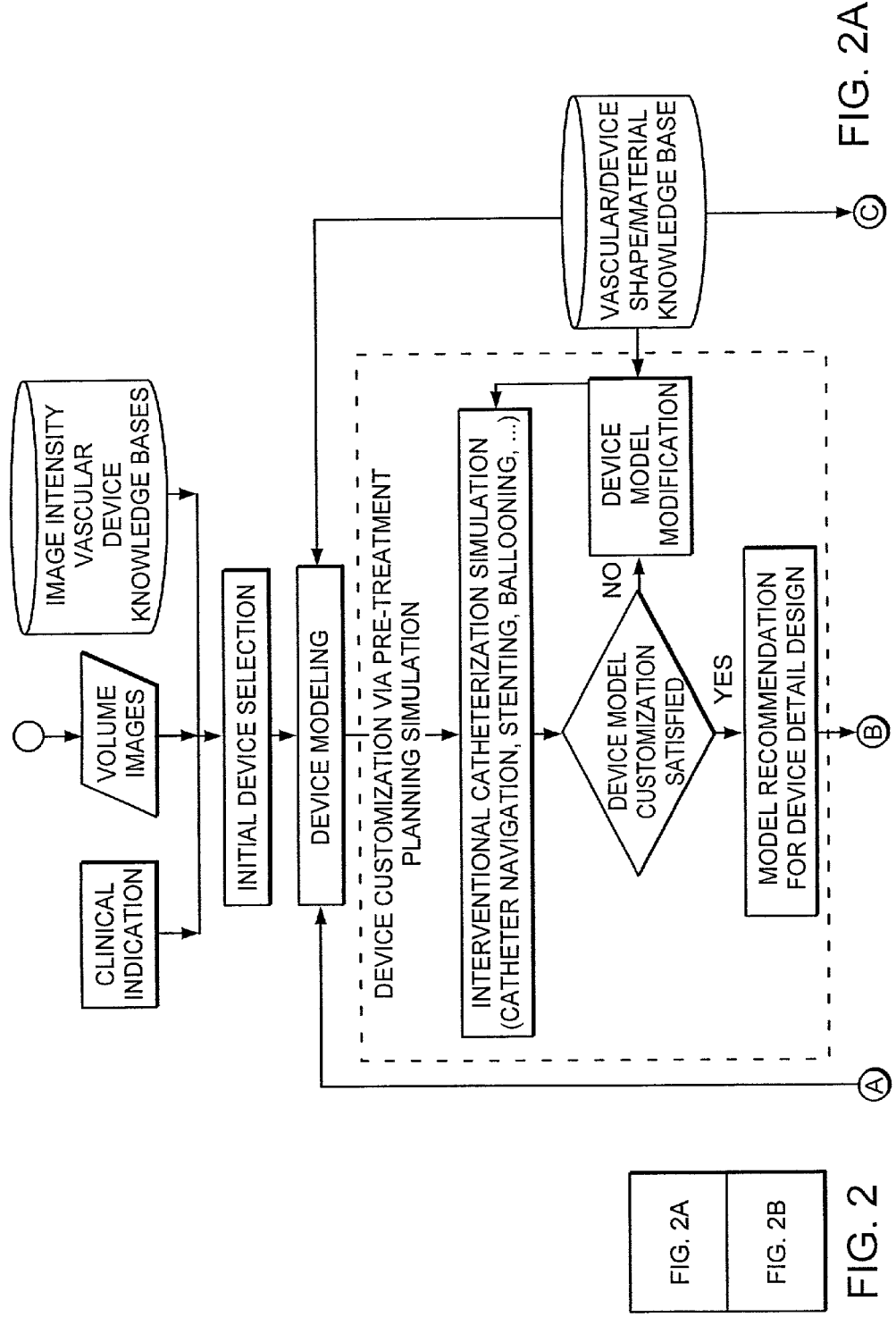

US 7,371,067 B2

SIMULATION METHOD FOR DESIGNING CUSTOMIZED MEDICAL DEVICES

RELATED APPLICATIONS

This application claims priority under 35 U.S.C. § 119(e) to U.S. Provisional Application Ser. No. 60/273,734 and to U.S. Provisional Application 60/273,733, both filed Mar. 6, 2001, the entireties of which are incorporated by reference herein.

FIELD OF THE INVENTION

The invention relates to a method and system for designing customized, patient-specific medical devices, particularly those used in image-guided medical procedures (e.g., such as vascular catheterization, angioplasty, stent, balloon, and coil placement).

BACKGROUND OF THE INVENTION

Recent progress in medical science and engineering has helped to reduce the use of traditional "open body" surgery in which incisions are made to provide access to the operating area within the human body. Minimally invasive therapy, a technique often performed on an outpatient basis without extended hospitalization, is becoming increasingly popular.

Cardiovascular Interventional Radiology, one of the most complex and patient care-oriented fields in radiology, is a medical specialty that uses image-guided, minimally invasive diagnostic and treatment techniques. Because interventional radiologists treat diseases non-operatively, procedures performed by interventional radiologists are generally less costly and less traumatic to a patient than surgery, involving smaller incisions, less pain, and shorter hospital stays. This can lead to improved quality of health care delivery, decreased recovery time and reduced total cost to the patient and health care payors.

Interventional cardiovascular radiology often requires the need to enter the vasculature through small incisions and to utilize medical image guidance to maneuver thin plastic tubes or catheters or other therapeutic or diagnostic devices to a target site in a human body. Most cardiovascular interventional procedures are performed using catheters which are extremely diverse in shape and specific features.

Specific catheter tip shaping generally is required because of the wide variety of sizes and anatomical configurations of blood vessels and because the vascular characteristics of lesion affecting blood vessels vary significantly between individuals. In the 1960s, before the availability of pre-formed angiographic catheters, Dr. Melvin P. Judkins shaped catheters at the time of each examination by placing a polyurethane tubing over a stiff wire bent to conform to the shape of the blood vessel and then immersing the catheter in boiling water to soften it. When the assembly cooled, he withdrew the wire, and the catheter retained its shape (see, e.g., as described in Dotter and Judkins, 1964, Circulation 30: 654-670; *The Catheter Introducers,* 1993, Eds: L. A. Geddes and L. E. Geddes, Mobium Press, Chicago, Ill., pp 46; Judkins, 1967, *Radiology* 89: 815-824). Although there are now many commercially available preformed catheters, clinicians still use steam heating and mandrels to modify the shape of a catheter's tip.

Currently, many years of clinical/design experience and considerable physical prototyping is necessary to create new interventional devices including catheters, guidewires, stents, stent grafts, coils and balloon therapy devices. Customization of devices is still done in an ad hoc fashion.

SUMMARY OF THE INVENTION

There is a need in the art to provide appropriate interventional devices for image-guided procedures such as vascular catheterization, the placement of stents and stent-grafts, as well as balloon and coil deployment. Because there is considerable variation in human anatomy and pathology, it is often not clear whether a particular device is the most appropriate for a specific patient. The goal of this invention is to create patient-specific medical devices. Preferably, the design of a device is evaluated and modified, if necessary, based on the behavior of the device when it is deployed in a simulated system representing the anatomy of a patient in which the device will be used. Though the intention is to create instruments targeted for specific patients, it is possible that a group of patients or similar pathologies also may be targeted if the degree of similarities between patients/pathologies is high and acceptable to the medical community.

In one aspect, the invention provides a method and system to design and evaluate the potential performance and/or clinical application of medical devices, such as in cardiovascular treatment methods. The design and evaluation process is based on a quantitative analysis of volume-rendered images of a body cavity or lumen of a specific patient. A geometric model of the cavity of lumen is obtained from this analysis and a system comprising one or more knowledge bases is used to derive the geometry, topology, and physical properties of the device from this model. Physical properties of the body cavity or lumen (e.g., such as elasticity, wall thickness and the like) also can be used to optimize device design parameters. Volume images can be obtained from one or more devices routinely used in clinical settings such as x-ray devices, magnetic resonance imaging (MRI) devices, ultrasound (US) devices, computerized tomography (CT) devices, rotational angiography devices, gadolinium enhanced MR angiography devices, or other imaging modalities. Preferably, the lumen of the patient is a blood vessel. In one aspect, the device is designed for a patient having a pathology (e.g., such as atherosclerosis) and the device is optimized for maneuvering and deploying in a lumen which has characteristics of the pathology (e.g., such as plaque formation).

A variety of devices can be designed using the method and system disclosed herein. Suitable devices which can be designed include, but are not limited to: a catheter, a guidewire, a balloon, a balloon-inflating device, a coil, a stent, a stent-graft, an endoscope, a laparoscope, a bronchoscope, a surgical device, a vascular occlusion device, an optical probe, and a drug delivery device. It should be obvious to those of skill in the art that a single device can have multiple design features or functions. For example, a catheter can also be configured as an optical probe and/or drug delivery device.

In one aspect, the invention provides a method for designing a medical device for accessing a body cavity or lumen of a patient comprising providing data relating to a three-dimensional geometric model of the cavity or lumen to a system comprising a knowledge base and obtaining a recommendation from the system relating to the geometry of a device for placement into the cavity or lumen. Preferably, the system comprises a knowledge base comprising a plurality of geometries for at least one segment of a device and rules for determining correspondence between a geometry of at least one segment and at least one portion of the body cavity or lumen. The recommendation made by the system can be in the form of a three-dimensional representation of the medical device, which is displayed on an interface of a user device connectable to the network.

Selectable options corresponding to design parameters of the device are transmitted to, and displayed on, the interface of the user device. Selectable options can include, but are not limited to: selectable buttons, drop-down menus, dialogue boxes, command lines, and the like, which can be used to select one or more device parameters such as shape, material, flexibility, shape memory, stiffness, softness, pliability, stability, strength, contrast medium flow rate, length, and size. Preferably, the system simulates the design of the device based on the one or more selected parameters. One or more feature operations can be performed to modify a recommended geometry, such as shape sweeping, extruding, holing, braiding, edge rounding and hub construction.

In one aspect, a medical device is designed in segments which are aggregated to provide the final design of the device. In this scenario, parameters of one or more of the multiple segments can be selected independently. For example, the system can be used to design a catheter by simulating a plurality of catheter segments, each segment corresponding to a different section of the catheter, such as the catheter's tip, a portion of the catheter's body, a hook element, hub element (e.g., for connection with a drug delivery system), or other features which may typically form part of a catheter. In one aspect, at least two of the segments being designed have different material properties.

In a preferred aspect of the invention, the system simulates a path which represents at least a portion of the body cavity or lumen and determines fit between the geometry of the device and the geometry of the path. In one aspect, the system displays a simulated device which fits into the path and a user of the system can select one or more of a plurality of selectable options displayed on the interface of the user device to alter one or more device parameters. The system can then modify the simulated device according to the one or more parameters selected and can a new device incorporating the one or more parameters.

In one aspect, the design of the device is validated by using an intervention simulation device with a system for simulating the contours of the body cavity or lumen. Preferably, this system also simulates various parameters that might be experienced by a user when maneuvering or deploying the device (e.g., such as cardiac contractions, blood flow, respiration, and the like).

The invention also provides a device simulation system which comprises a user device (e.g., a computer or wireless device connectable to the network) comprising a graphical user interface, a processor for generating a geometric model from volume-rendered images, and one or more knowledge base systems for obtaining data from the geometric model and for producing a device geometry based on the model. Preferably, the system comprises an expert system for identifying relationships between data in the knowledge base and data relating to the images.

In one aspect, the system comprises a device shape knowledge base comprising: a plurality of geometries for at least one segment of a device; and rules for determining correspondence between a geometry of the at least one segment and at least a portion of a model of the body cavity or lumen. The knowledge base transmits data relating to the one or more device segment geometries (e.g., in the form of a graphical representation of the device) to the user interface upon receiving data relating to the geometry of the cavity or lumen (e.g., in the form of a graphical representation of the cavity or lumen). Preferably, the system also comprises a device materials knowledge base comprising a plurality of data files relating to device materials and rules for determining suitability of a device material for at least one segment of the device.

The knowledge base system also can comprise one or more data files relating to physical properties of the anatomy of the patient and/or substantially similar patients, or relating to clinical data obtained for the patient and/or for a population of patients. The system additionally may include one or more scanning devices for obtaining scanned volume images, such as x-ray devices, MRI devices, US devices, CT devices, rotational angiography devices, gadolinium enhanced MR angiography devices, and the like. Preferably, the system comprises a means for feature extraction and has analysis capabilities such as FEM meshing, computation, searching and measurement. In one aspect, the system is capable of performing a goal-driven search of the knowledge base to recommend a device geometry, which optimally corresponds to the model of the cavity or lumen in response to a user query. The system also can display rules used for making particular device recommendations in response to a user query.

The invention further provides a software suite for use with the system comprising a first component for storing a device shape knowledge base which comprises a plurality of geometries for at least one segment of a medical device and rules for determining correspondence between the geometry of the at least one segment and at least a portion of a geometric model of the body cavity or lumen. The suite also comprises a second component comprising an executing function for executing one or more programs for determining whether one or more of the geometries of the at least one segment corresponds to the geometric model of at least a portion of the body cavity or lumen based on the rules for determining correspondence. Preferably, the software suite also comprises a third component for interfacing with a user device which provides a retrieval function for retrieving data relating to a geometric model of at least a portion of the body cavity or lumen and a transmitting function for transmitting the data to the knowledge base.

BRIEF DESCRIPTION OF THE FIGURES

The objects and features of the invention can be better understood with reference to the following detailed description and accompanying drawings.

FIG. 8A shows virtual catheter navigation and stenting.

DETAILED DESCRIPTION

Figure 1:
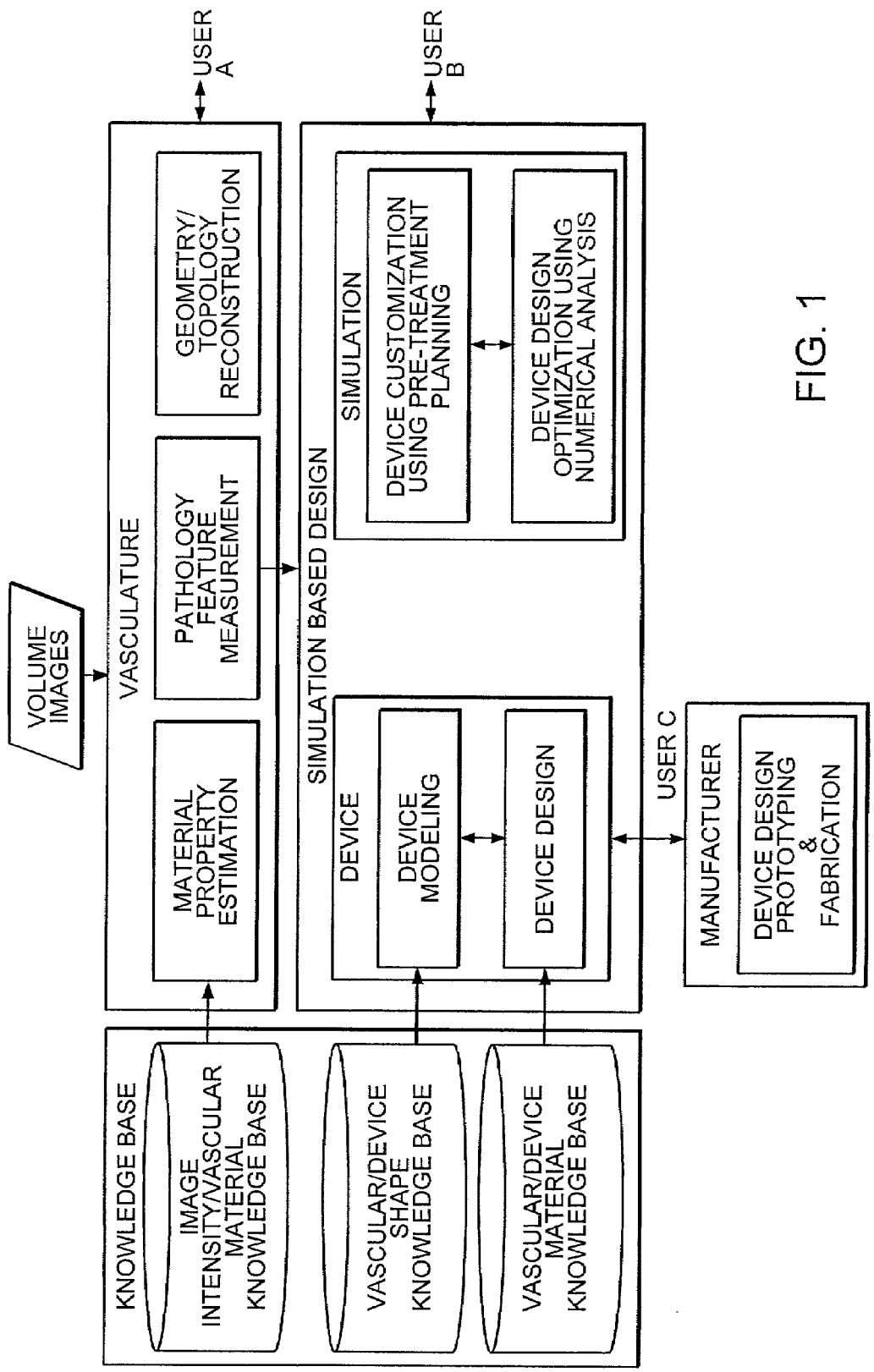
FIG. 1 is a schematic diagram showing the architecture of the system according to one aspect of the invention. Volume images acquired from MRA, CTA, ultrasound, DSA, or XRA scanning of a patient are inputted into the system. Different groups of professionals (User A, User B, and User C) having different skill sets can be involved in different aspects of the design of a device.
Figure 2B:
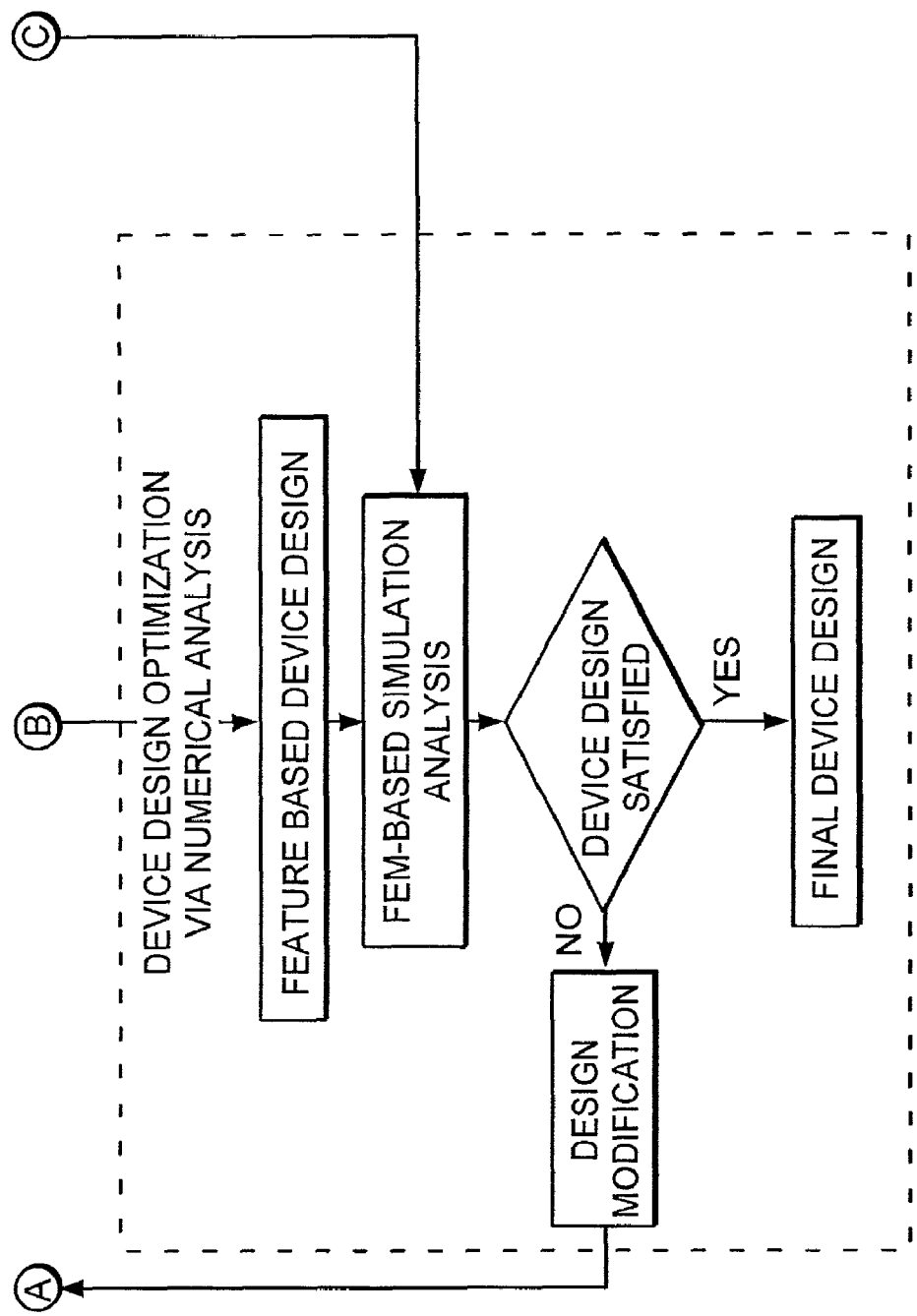
FIG. 2 is a flow chart showing a method of using the system according to the invention to design a customized interventional medical device.

The invention is designed to provide more effective mechanical prototyping of medical devices, particularly cardiovascular interventional devices, such as catheters, guidewires, balloon therapy catheters, stents, stent grafts, and vascular occluding devices. The invention utilizes a medical image-based simulation technique for computer-assisted design of interventional devices and provides a system for implementing the technique. Devices can be used for patient-specific applications as well as for more generic patient population use.

Definitions

The following definitions are provided for specific terms which are used in the following written description.

As used herein, "a volume image" is a stack of two-dimensional (2D) images (e.g., of a body cavity or lumen) oriented in an axial direction.

As used herein, a device for "accessing a body cavity or lumen" refers to a device which can be maneuvered in the body cavity or lumen. "Maneuvering" refers to the ability of at least about 50% of the external surface of the device to fit within a cavity or lumen while retaining rotational or forward translational freedom of movement.

As used herein, an "interventional medical device" includes a device for treatment (e.g., stents, stent-grafts, balloons, coils, drug delivery devices), for diagnosis (e.g., imaging probes), and for placement of other medical devices (e.g., guidewires). Some devices, such as catheters, can have multiple functions. In general, the terms "an interventional medical device" and "device for accessing a body cavity or lumen" are used interchangeably.

As used herein, a "knowledge base" is a data structure comprising facts and rules relating to a subject; for example, a "device shape knowledge base" is a data structure comprising facts relating to geometries for each of a plurality of segments of one or more medical devices and rules for relating these geometries to the geometry of at least a portion of a body cavity or lumen.

As used herein, a "rule" in a knowledge base refers to a statement associated with a certainty factor. Rules are generally established by interviewing human experts or by obtaining data from databases or other knowledge bases.

As used herein, "rules for determining the suitability of a device material" refer to rules which associate a particular device material with particular types of body cavities or lumens within which at least a segment of the device comprising the material will be maneuvered.

As used herein, an "expert system" comprises a program for applying the rules of one or more knowledge bases to data provided to, or stored within the knowledge base(s), thereby enabling the knowledge base(s) to be queried and to grow. Preferably, an expert system comprises an inference engine which enables the system to manipulate input data from a user to arrive at one or more possible answers to a question by a user. More preferably, an expert system also comprises a cache or dynamic memory for storing the current state of any active rule along with facts relating to premises on which the rule is based.

As used herein, "a physical property" refers to a property which relates to the structure or anatomy of a body cavity or lumen which is measurable, generally without the aid of a labeled molecular probe; for example, physical properties of a blood vessel include, but are not limited to: elasticity, thickness, strength of ventricular contractions, vascular resistance, fluid volume, cardiac output, myocardial contractility, and other related parameters.

As used herein, a pathology "affecting the structure of the body cavity or lumen" is one which measurably alters at least one physical property of the body cavity or lumen.

As used herein, "a segment of a device" is a representation of a three-dimensional portion of a device (which may be graphical or in the form of data points). Generally, the dimensions of a segment are defined by a user. Generally, the dimensions of a segment are scaled to the standard size of commercial medical devices. For example, a segment can have a cross-sectional outer diameter of about 3 mm.

As used herein, a "segment which corresponds to a portion of a device" is a three-dimensional representation of a portion of a device which is of the same scale as the portion of the device.

As used herein, "obtaining a recommendation from a system comprising a knowledge base relating to the geometry of a device" refers to obtaining an output from a system in the form of a volumetric dataset. Preferably, the data in the data set exists in a "virtual" coordinate space which accurately reflects real-world dimensions of at least a segment of the device, at least with respect to scale, if not actual dimensions.

As used herein, a system which "simulates a path representing at least a portion of a body cavity or lumen" is a system which displays a three-dimensional representation of the internal surface of the at least a portion of the body cavity or lumen on the interface of a user device in communication with the system.

As used herein, to "determine the fit between the geometry of the device and the geometry of the path" refers to displaying a representation of at least a portion of the device and simulating its placement within at least a portion of the body cavity or lumen.

As used herein, "a feature operation" is an operation to modify a shape parameter of at least one segment of a virtual representation of a device.

As used herein, a "device parameter" refers to a physical property of a device, e.g., such as flexibility, memory, material, shape, and the like.

As used herein, "a physical model of a device" is a combination of the recommended geometrical model, topology, and material. It is also the basis for making the first design of a medical device based on patient-specific data.

As used herein, a "software suite" refers to a plurality of interacting programs for communicating with an operating system.

As used herein, "coupled to" refers to direct or indirect coupling of one element of a system to another. An element may be removably coupled or permanently coupled to another element of the system.

As used herein, "within scanning distance" refers to a distance which is close enough to the manikin to permit display of an image of the simulated body cavity or lumen on the scanning display of the system.

As used herein, "a re-configurable control panel" refers to a display interface comprising one or more selectable options (e.g., in the form of action buttons, radio buttons, check buttons, drop-down menus, and the like) which can be selected by a user and which can direct the system to perform operation(s). Preferably, the one or more options can be selected by touch. The control panel can be modified by a user (e.g., by implementing a system program which alters the display, causing it to display different selectable options) thereby "re-configuring" the control panel.

As used herein, "providing access to a database" refers to providing a selectable option on the display of a user device which, when selected, causes the system to display images or data stored within the database, or causes one or more links to be displayed which, when selected, causes the system to display the images or data. In one aspect, the system displays images or data, or links to images or data, in response to a query of the system by a user. In one aspect, the display interface provides a "query input field" into which the user can input a query and the selectable option is an action button for transmitting the query to the system.

As used herein, the term "in communication with" refers to the ability of a system or component of a system to receive input data from another system or component of a system and to provide an output response in response to the input data. "Output" may be in the form of data or may be in the form of an action taken by the system or component of the system.

As used herein, "deployment of a balloon" refers to either inflation or deflation of the balloon.

As used herein, a pathology "affecting the structure of the body cavity or lumen" is one which measurably alters at least one physical property of the body cavity or lumen.

As used herein, "a physical property" refers to a property which relates to the structure or anatomy of a body cavity or lumen which is measurable, generally without the aid of a labeled molecular probe; for example, physical properties of a blood vessel include, but are not limited to: elasticity, thickness, strength of ventricular contractions, vascular resistance, fluid volume, cardiac output, myocardial contractility, and other related parameters.

As used herein, "clinical data" refers to physical, anatomical, and/or physiological data acquired by medical image modalities such as X-ray, MRI, CT, US, angiography, video camera, or by direct physical and/or electronic measurements.

As used herein, "a best fit" between a simulated path for a simulated body cavity or lumen and a simulated medical device refers to one which requires the minimum amount of deformation in the simulated surgical process that takes into consideration the patient-specific vasculature and composite materials of the device.

As used herein, an "FEM engine" refers to a program or set of programs for performing finite element analysis focusing on vasculature finite element models and analysis of the interaction between vasculature models and devices.

System Components

The invention provides a system for designing a medical device for accessing a body cavity or lumen of a patient. The invention also provides a device simulation system for performing the method which comprises a user device (e.g., a computer or wireless device connectable to the network) comprising a graphical user interface, a processor for generating a geometric model from volume-rendered images ("geometric modeling system") and one or more knowledge bases for obtaining data from the geometric model and for producing a device geometry based on the model. Preferably, the system comprises an expert system for identifying relationships between data in the knowledge base and data relating to the images.

The system operates by means of a software suite that operates on a general purpose computer such as a PC or IBM-compatible device. Preferably, the system comprises a processor (e.g., as CPU), memory, graphics adaptor, printer controller, hard disk and controller, mouse controller, and the like. The processor should comprise a minimum of about 8 MB of RAM. Preferably, the user display interface is part of a monitor which is connected to a keyboard, mouse, and, optionally, printer and/or scanning device. The software suite of the system comprises a program (e.g., a C language program) which controls the system's user interface and data files and one or more sets of knowledge bases, allowing various components of the system to interact with each other.

Geometric Modeling System

Figure 3:
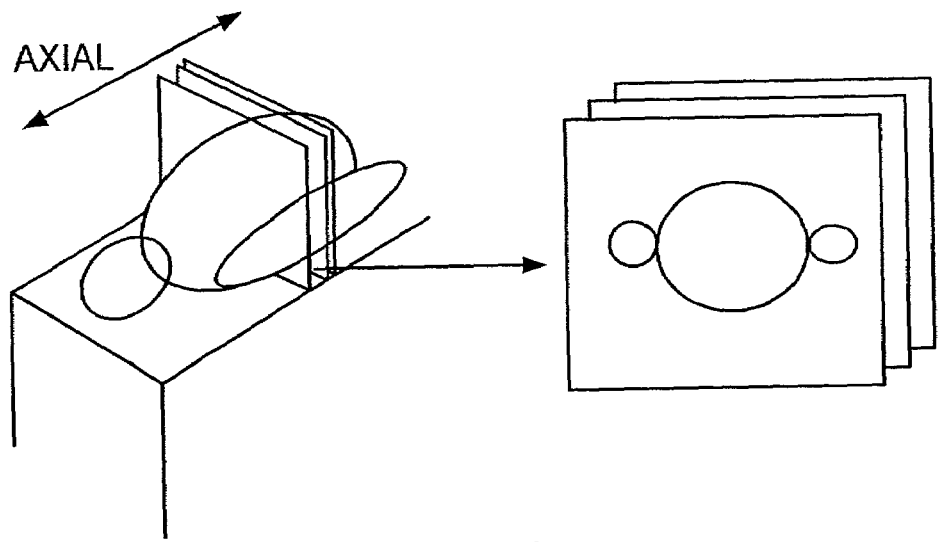
FIG. 3 is a schematic diagram of scanned images of a body being used to create a volume image. The left side of the Figure shows the collection of a plurality of scanned images. The right side of the Figure shows how scanned images can be combined to create a volume image.
Figure 4:
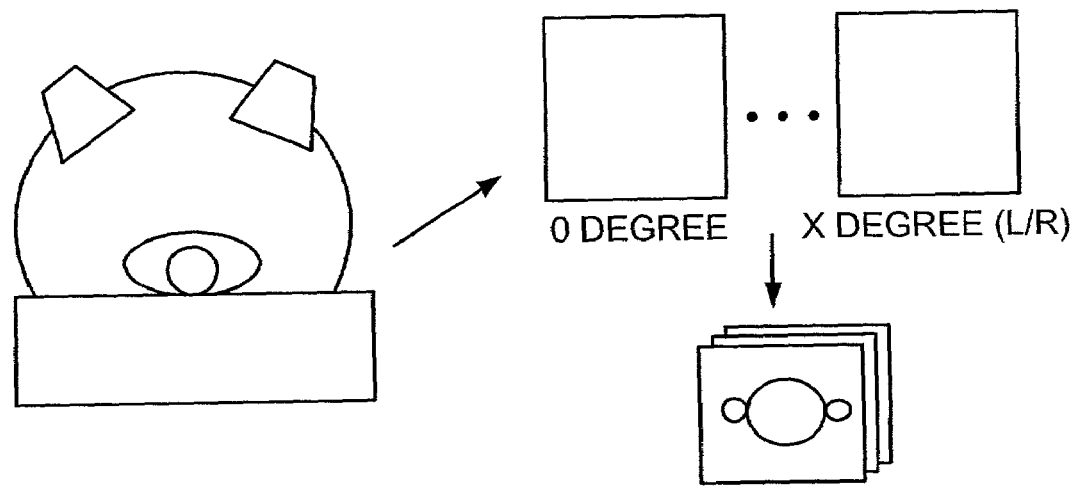
FIG. 4 is a schematic diagram showing the use of a Filtered Back Projection technique or Arithmetic Reconstruction Technique (ART) in one aspect according to the invention.

In one aspect, optical data relating to the internal contours of a body cavity or lumen are obtained and provided to the device simulation system. Generally, a stack of two-dimensional (2D) images is collected by a scanning device in an axial direction and is used to form a three-dimensional (3D) structure or volume image (see, e.g., as shown in FIGS. 3A and 3B). Almost all medical scanners can produce these axial images or can produce images that can be converted easily to axial images. Suitable scanning devices include, but are not limited to, x-ray devices, magnetic resonance imaging (MRI) devices, ultrasound (US) devices, computerized tomography (CT) devices, rotational angiography devices, gadolinium-enhanced MR angiography devices, or other imaging modalities. For example, rotational CT scanners capture patient data in the form of projection images. By using a Filtered Back Projection technique or Arithmetic Reconstruction Technique (ART), volumetric images can be constructed. This method is illustrated in FIG. 4.

The system may be directly connected to the output of one or more scanning devices, e.g., receiving optical data from such devices as these are acquired. However, in another aspect, the system may include a means for extracting features from individual scanned images (e.g., communicated to the system through a scanner or provided as a pdf file) to construct a 3D volume image. The geometric modeling arm of the system (see FIG. 1, "Vasculature") can be implemented remotely by a user A to determine one or more of: the geometry/topology of the body cavity or lumen, measurements relating to any pathological features of the body cavity or lumen, and such parameters as tissue wall thickness, elasticity and the like ("Material Property Estimation" in FIG. 1).

In creating a geometric model of a body cavity or lumen (e.g., such as a blood vessel), a user A of the system (e.g., a biomedical professional with knowledge of human anatomy and pathology) performs image processing tasks on a plurality of scanned images to create geometrical structures and a topology which corresponds to the contours of a body cavity or lumen belonging to a specific patient being analyzed.

Volume rendering techniques such as ray casting and projection techniques have traditionally been used in the visualization of volume images. Ray casting methods shoot rays through a volume object from each pixel in an image and employ algorithms that trilinearly interpolates samples along each ray, providing complex shading calculations and color assignments at the sample points which are then accumulated into final pixel colors (see, e.g., Kaufman, In *Volume Rendering*, IEEE Computer Science Press, Las Alamitos, Calif., 1990). Real-time volume rendering with hardware texture mapping (e.g., SGI) for UNIX platform or with board card (e.g., Mitsubishi VolumePro) for PC platforms are commercially available.

Commercially available image processing tools, such as Photoshop™ can be used to manually draw out the shape of the structure from each scanned image. Various imaging processing tasks, as are known in the art, can be performed by the system; for example, segmentation can be used. Several improved algorithms using iso-surfacing or volume-rendering techniques to visualize vascular trees also can be used and have been described in Ehricke, et al., *Computer & Graphics* 18(3): 395-406, 1994; Cline, et al., In *Magnetic Resonance Imaging* (Pergamon Press) 7: 45-54, 1989; and Puig, et al., *Proc. Of Visualization '97*, pp 443-446, for example.

Projection-originated methods reconstruct 3D geometries from two or more images (See, e.g., Solbach, et al., *Computer Biomedical Research* 27(3): 178-198, 1994; Nguyen and Sklansky, *IEEE Transactions on Medical Imaging* 13(3): 178-198, 1994; Longuet-Higgens, *Nature* 293(10): 133-135, 1981). Thinning methods such as "active-contour", "medial axis transformation", and "simulated annealing", and the like, can be employed to determine information in projection planes (see, e.g., Kass, et al., *International Journal of Computer Vision* 1: 321-331, 1987; Lee, et al., *CVGIP: Graphical Models and Image Processing* 56(6): 462-478, 1994; Arcelli and di Baja, *Image and Vision Computing* 11(2): 163-173, 1993; Pellot, et al., *IEEE Transactions Medical Imaging* 13(1): 48-60, 1994; Brandt and Algazi, *CVGIP: Image Understanding* 55(3): 329-337, 1992). The advantage of projective reconstruction lies in its capability to handle tiny tube-like systems such as vascular, neural and lymphatic vessels that could be lost with iso-surfacing algorithms.

"Piece-by-piece cylinder representation" or "generalized cylinder representation" is widely used in vascular modeling (see, e.g., Brown et al., *Proceedings of EUROGRAPHY '87*, pp 113-124;Barillot et al., *IEEE Transactions on Computer Graphics and Applications*, December 1985, pp 13-19). Polygonal tessellation, e.g., triangulation, also can be applied to model 3D tube-like shapes as is known in the art (see, e.g., Sederberg, et al., *International Journal on Computational Geometry and Applications* 8(4): 389-406; Choi and Park, *Visual Computer* 10: 372-387, 1994). Ferley, et al., *Computer Graphics Forum* 165(5): 283-293, 1997, additionally describes an implicit surface method for reconstruction of branching shapes.

Figure 5:
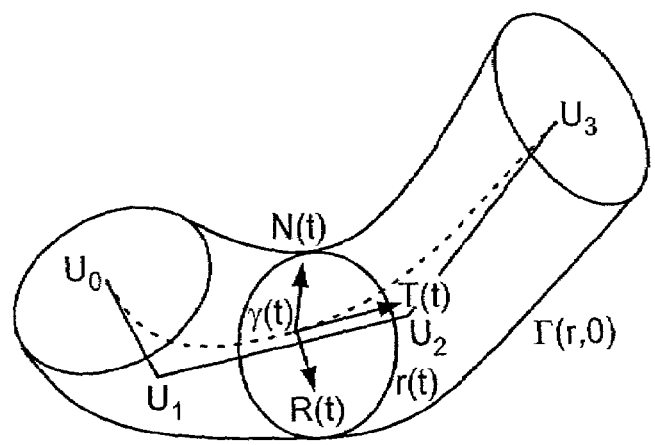
FIG. 5 is a schematic diagram of a geometric model of a volume image obtained by tubular surface sweeping according to one aspect of the invention.
Figure 6:
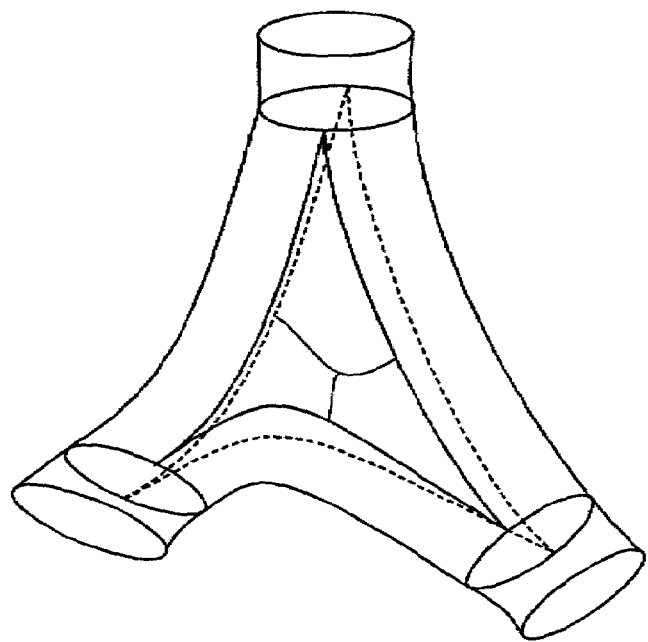
FIG. 6 is a schematic diagram of a geometric model of a volume image obtained by bifurcation sweeping according to one aspect of the invention.
Figure 7:
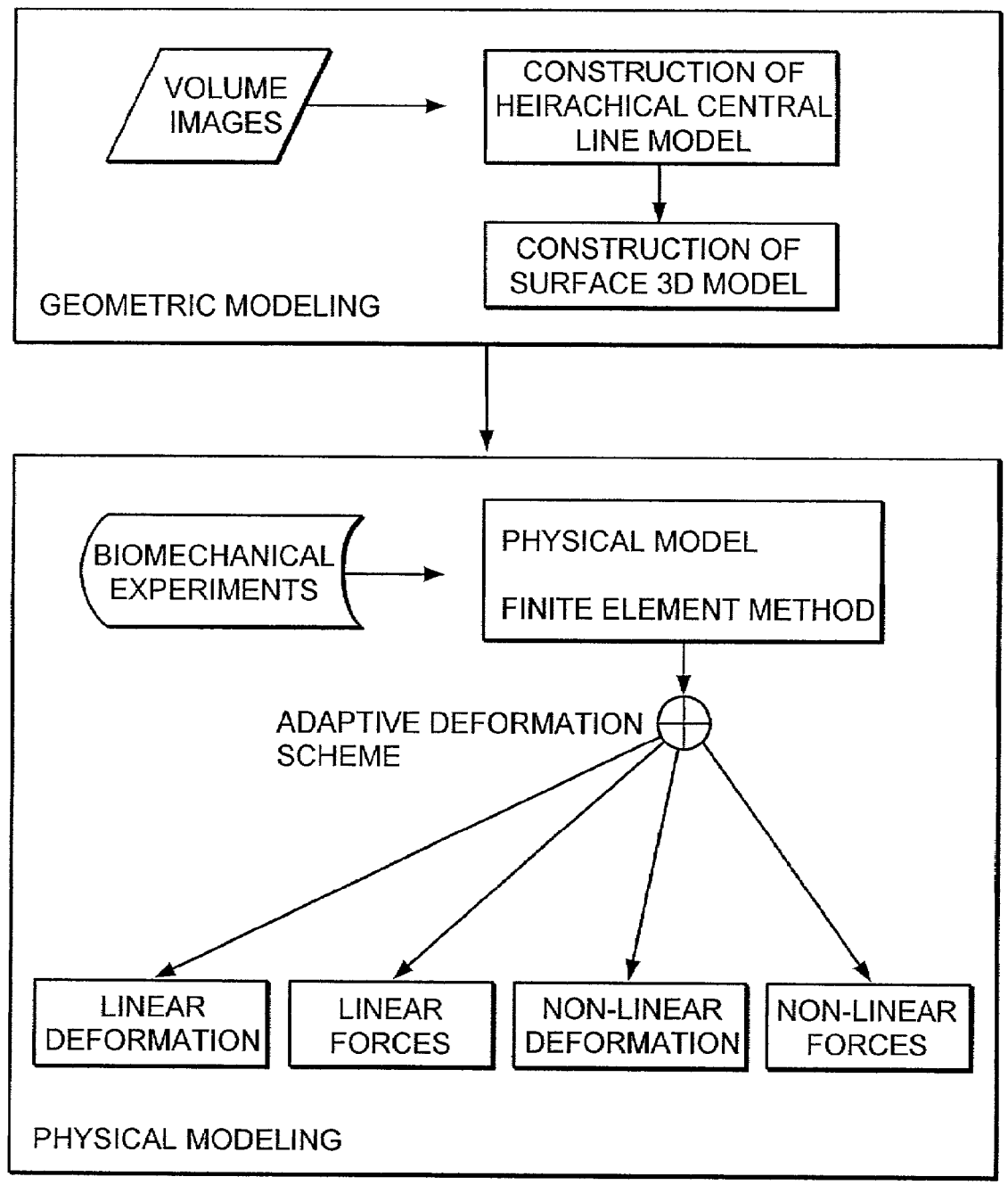
FIG. 7 is a flow chart showing a method for creating a geometrical vascular model reconstructed from a three-dimensional medical image and application of a deformation-law to model the effects of the interactions between a medical device and body lumen.

Accurate modeling of a 3D vascular network relies on good representations of vascular segments and bifurcations. Ideally, a vascular model should be visually smooth and the detail of the display should be adaptable to fit application requirements. In one aspect, a constructive approach is used to model visually smooth vascular networks. In this approach, vascular segments are modeled using sweeping operations while vascular bifurcations can be modeled using blending operations (i.e., sweeping plus hole-filling operations) (Gregory and Zhou, *Computer Aided Geometric Design* 11: 391-410, 1994; Ye, et al., *Computer Aided Geometric Design* 27: 875-885, 1995). Based on GC conditions for boundaries and cross-boundary derivatives (see, e.g., Schreiner and Buxbaum, *IEEE Transactions on Biomedical Engineering* 40(5): 482-491, 1993), constructive algorithms for segmental sweeping and bifurcation blending can be designed as described in Cai et al., "Constructive Algorithms for GC1 Generation of Vascular Network," Submitted to IEEE Biomedical Engineering, March 2001. See, as shown in FIGS. 5 and 6.

Yet another method of obtaining a volume model or a geometric model of a body cavity or lumen is the technique of volumetric meshing. Meshes which represent a 3D or volumetric form can be generated from scanned images using a standard Windows operating system such as NT. Software for generating 3D mesh images are commercially and publicly available. Sources for such software are described at http://www-users.informatik.rwth-aachen.de/~roberts/software.html#Commercial, and include, for example, Altair®HyperMesh®5.0 (available from Altair Engineering, Inc., Maplelawn, Troy, Mich. 48084).

In a preferred aspect, a volume image of a blood vessel is obtained to construct a physical or geometric model which comprises information relating to both shape and material of tissue forming the blood vessel. Generally, construction of geometric models entail dividing a 3D modeling process into a series of 2D cross-sectional segmentation operations from which the 3D surface of the structure is reconstructed. An image processor is used to draw out the shape of the desired vascular structure from each image. Segmentation methods relying on intensity thresholding or region-growing can be used, as are known in the art, to facilitate the process (see, e.g., Wang, et al., *IEEE Engineering in Medicine and Biology*, November/December 1999, pp 33-39; Moore, et al., *J. Biomechanics* 31: 179-184, 1998). Finite element modeling also can be used for blood flow modeling, as described in, for example, Taylor, et al., *Computer Methods in Applied Mechanics and Engineering* 158: 155-196; Hughes et al., *Computer Methods in Applied Mechanics and Engineering* 73(2): 173-189, 1989; Shephard and Georges, *Int. J. Numerical Methods in Engineering* 32: 709-749, 1991.

Surface sweeping is a powerful tool for creating tube-like shapes, i.e., simulating blood vessels. The sweeping operation requires a smooth trajectory and cross-sectional shapes. To form a tube-like surface, a closed cross-sectional contour must be used. A cubic Bézier curve is used to represent the central trajectory or path. With $\gamma(t)$ representing any of $G^I$ paths, a local coordinate system $(T(t), N(t), B(t))$ can be defined along the curve (see, e.g., FIG. 5). This triplet $(T(t), N(t), B(t))$, also known as a "Frenet frame", is the tangent, normal and bi-normal defined along the trajectory of the curve. Assuming $r(t)$ is a contour function defined in the cross-sectional plane perpendicular to the curve at a given point along the trajectory, the sweeping surface can be represented as $$\Gamma(t,\theta) = \gamma(t) + r(t)(\cos\theta N(t) + \sin\theta B(t)),$$

as described by Piegl and Tiller, In *The NURBS Book*, Springer, Berlin, 1995, where $\theta$ is the cross-sectional angle and $t \in [0,1]$ is a parameter defined along the curve. A bi-cubic Bézier form for the sweeping tube can therefore be developed using a tensor-product operation (see, e.g., Piegl and Tiller, 1995, supra).

To model bifurcation, the same sweeping operation can be applied. In order to avoid self-intersection, only half of the tubular surface can be used (FIG. 6). This, however, leads to missing two triangular patches (front and back) at the joint. Bifurcation modeling therefore requires triangular hole filling. An analytic approach described in Gregory and Zhou, *Computer Aided Geometric Design* 11: 391-410, 1994, can be used to fill triangular holes with given neighboring surfaces. To generate $G^1$ smooth bifurcations, however, additional modifications of hole boundaries and hence the surrounding surfaces are desirable. The procedures for bifurcation modeling are summarized as follows:

(i) A bifurcation is first generated by sweeping three semi-tubular surfaces in bi-cubic Bézier form.

(ii) Two triangular holes are formed by three surrounding semi-tubular surfaces. Each hole is initially "filled" with three bi-cubic Bézier patches using the method described in Gregory and Zhou, 1994, supra.

(iii) The boundaries of the semi-tubular surfaces are changed to quintic Bézier form. The modifications are determined from the cross-boundary tangential continuity, twist-compatibility and unique existence of tangent planes at hole corners.

(iv) Three semi-tubular surfaces are then degree-elevated into quintic Bézier patches and modified based on the new hole boundaries. The next row of control points of the hole boundaries are modified accordingly to ensure that the semi-tubular surfaces having cubic cross-boundary derivatives along the hole boundaries.

(v) The vector-valued cross-boundary derivative in a quintic form along the hole boundaries is generated for the filling hole patches.

(vi) The hole boundaries are split into two at the middle point of the parameter, so are the associated vector-valued cross-boundary derivatives. The star-lines and their associated vector-valued cross-boundary derivatives are degree-elevated to quintic as well.

(vii) Three final filling rectangular patches are generated based on the updated starlines, split hole boundaries, and the vector-valued cross-boundary derivatives along the star-lines and the split hole boundaries. The remaining 3×3 interior control points are determined by taking a Coons-Boolean sum approach as described in Ye, *Computer Aided Design* 27: 875-885; 1995.

From the segmented medical images, a central line model of a vasculature can be constructed. This model is represented in hierarchical structure consisting of vessel topology (using a parent-child relationship to represent the topological connectivity among a list of a vascular segments), vessel geometry (coordinates and radii), and vessel material property. The 3D model of the vessels is then reconstructed based on the central line geometry. Visual smoothness is achieved by employing operations like sweeping and blending. A variational modeling approach is implemented for vasculature segments. An advantage of such method is that it provides flexibility in changing 3D structure. Where a pathology is identified and measured, a vascular model can be modified to account for the pathology.

Preferably, deformable models are used to detect structures in images. Such models can be used to define a geometry which minimizes the energy of a simulated structure to account for topological change, e.g., due to factors such as blood flow dynamics and even interactions between the device and the body lumen or cavity. For example, catheter tip shape deforms in a predictable manner when straightened with a guide wire, when advancing through tortuous vessels, and when encountering vascular constraints such as lumen narrowing, branch point bifurcations, and the like. These events can be modeled using the simulation system.

In one aspect, a deformation law is applied to a geometric model obtained from a hierarchical central line model to construct a 3D model. This 3D model can be used to model linear deformation, linear forces, non-linear deformation, and non-linear forces. The application of deformation laws to a geometric model is described in, for example, Wang, et al., 1999, supra, Mallaldi, et al., *J. Mathematical Imaging and Vision* 6(2-3): 269-289, 1996; Caselles et al., *Numerische mathematik* 66: 1-31, 1993; Osher and Sethian, *J. Computational Physics* 79: 12-49, 1988; Sethian, In *Level Set Methods*, Cambridge University Press, Cambridge, England, 1996, Caselles et al., *Int. J. Vis.* 22(1): 61-79; Kichenassamy et al, *Proc. 5$^{th}$ Int. Conf. Computer Vision*, pp. 810-815, 1995).

Knowledge Bases

Preferably, the system comprises an expert system (e.g., such as Nexpert Object, available from Neuron Data, Inc. of Palo Alto, Calif.).). The expert system provides a program for applying the rules of one or more knowledge bases to data added to or stored within the knowledge base(s). This enables the knowledge base to be a dynamic component of the device simulation system which can be queried and which grows as it is queried and as new facts are provided.

Preferably, the expert system comprises an inference engine which enables the system to manipulate input data from a user to arrive at one or more possible answers to a question by a user (e.g., one query might be to identify a suitable catheter material for a device or device segment navigating a portion of a blood vessel with a selected elasticity). More preferably, an expert system also comprises a cache or dynamic memory for storing the current state of any active rule along with facts relating to premises on which the rule is based.

In one aspect, the system comprises a device shape knowledge base which is a data structure comprising facts relating to geometries for each of a plurality of segments of one or more medical devices and rules for relating these geometries to the geometry of at least a portion of a body cavity or lumen. Data and index files for the knowledge base may be created on a personal computer of the system (e.g., comprising the user display interface) with a database management system as is known in the art. Rules in the knowledge base generally are established by interviewing human experts or by obtaining data from databases or other knowledge bases. For example, facts relating to geometries of segments of devices can be obtained from images or design specifications of commercially available medical devices or from models of newly simulated devices which become part of the knowledge base.

In one aspect, the system is used to simulate the design of a catheter. Catheters are plastic tubular devices with varying cross sections to facilitate their entry into particular types of lumens. Preferably, facts relating to geometries of segments of a plurality of commercially available catheters are stored in the device shape knowledge base. Such facts include data relating to the geometries of a plurality of catheter hubs and tips, as well as the geometry of catheter body segments, hook elements and the like. The rules in this knowledge base provide paradigms for matching particular geometries to particular models of body cavities or lumens (e.g., such as vascular models).

In one aspect, the device shapes database comprises curve shapes for commonly used guiding and diagnostic catheters, along with information on the vasculature and pathology with which they will interact. Based on the input vascular model (e.g., provided to the system from a user A), the system will display one or more shapes of a catheter to be used on the interface of the user device. The user can select one of the curve shapes from the recommended list.

Aspects of geometry which can be described in the knowledge base include external and internal diameters and length. Internal diameter of a catheter can be specified either by actual diameter (in thousands of an inch) or by the maximum diameter of a guidewire (in millimeters) which can be passed through the catheter. External diameter is generally expressed in French sizes, which are obtained by multiplying the actual diameter in millimeters by 3.0. In one aspect, rules for determining correlations between wall thickness and catheter properties, such as contrast flow rates, are stored in the database. French sizes from 5 through 8 are commonly used for diagnostic angiography.

Data relating to catheter length also can be stored in the knowledge base. Preferably, a catheter ranges from about 50 to 150 cm in length. Length variations will depend on the configuration of the catheter being designed, as well as its purpose and route of insertion (e.g., brachial vs. femoral). For example, pigtail catheters generally are about 110 cm in length whereas Judkins catheters are about 80 or 100 cm in length.

The user can configure the catheter by entering basic parameters on the display interface or the user can have the system decide basic parameters.

In another aspect, the device simulation system also comprises a device material knowledge base. This knowledge base includes information enabling the system to predict interactions between a device being simulated and the anatomy or pathology of a patient. In addition to providing initial recommendation on the materials of the device model, this knowledge base also is used to help refine the physical properties of the device in the simulation process.

For example, facts relating to the properties of catheter materials can be stored in the materials knowledge base included in the system. Suitable catheter materials include, but are not limited to, plastics, such as polyethylene (PE), polyurethane (PU), nylon, Teflon® and combinations thereof. The selection of particular catheter materials or combinations of materials will influence such properties pliability, torqueability, and shape memory.

For example, PE and PU impart very different characteristics to a catheter. Both are thermoplastic materials. PE is relatively resistant to the softening effect of radioopaque material, but can be softened by heating to allow reshaping for special tip configurations. PE is more easily extruded over other catheter layers. Due to its heat instability, PE must be gas sterilized, while PU, being less resistant to heating, is reported to provide a catheter with better memory and yet is a softer material due to more random molecular alignment. This softness is particularly desirable at a catheter's tip to reduce risk of arterial trauma during selective positioning.

Additional facts relating to catheter design can be stored in the materials knowledge base or in additional knowledge bases. Design parameters which can be selected include: axial or torque control (ability of the catheter to transmit rotational forces from the end of the catheter to its tip); forward motion control (ability to directly transmit force from the hub of the catheter longitudinally to its tip); maneuverability (ability to advance a catheter around sharp bends); flexibility (bendability on contact with a resistant surface); memory (ability of a catheter to recover and maintain a specific configuration after insertion and guidewire removal); stiffness (ability of a catheter to resist bending against flexibility);. softness (ability of a catheter to easily bend, incorporates flexibility and implies poor stiffness and poor memory); trackability (ability of a catheter to follow a guidewire along its course through the vascular anatomy; a combination of flexibility and pushability); pliability (ability of a catheter to bend and to be shaped); stability (ability of a catheter to remain in a position—a function of stiffness, memory, and matching of the catheter's configuration to the anatomy of the patient); strength (ability to withstand high pressure injections) and contrast medium delivery or maximum flow rate (ability to deliver high contrast material flow rates within a specified injection pressure range).

For each of the design parameters described above, correlations can be identified between values for the parameters and properties of the catheters and these can be stored in the materials knowledge base. For example, pliability is related to the stiffness of the plastic forming the catheter. Therefore, in one aspect, the materials knowledge base comprises data files relating the stiffness of a plurality of different plastics to pliability. The knowledge base also can be used to model the effect of placing thin wires in the lumen of the catheter on the stiffness of the catheter and/or on pliability. Because increased stiffness can decrease the maneuverability of a catheter, the stiffness of the plastic also can be correlated with the ability of a user to position the simulated catheter in some simulated anatomical configurations not perfectly matched to the catheter shape.

In a further aspect, the system comprises yet another knowledge base, relating to the physical and/or biological properties of the body cavity or lumen itself. Facts within this "vascular material knowledge base" can be derived in part from the geometric modeling arm of the device simulation system as well as from public databases (e.g., such as PubMed®) (see, as shown in FIG. 1). In one aspect, the property of elasticity can be established from the relationship between image density (determined from a volume image) of a portion of a body cavity or lumen and the stiffness of a particular tissue. In another aspect, the diameter of a cavity/lumen can be determined.

For example, plaque can be distinguished from vessel walls by evaluating the image intensity of a volume image. Preferably, as volume images of body cavities or lumens are acquired from patients having a disease, data relating to these images are provided to one or more of the knowledge base systems described above. Preferably, the knowledge base system(s) include data from images are obtained from patients having atherosclerosis, coronary vascular lesions, carotid bifurcation stenosis, carotid bifurcation stenosis, abdominal aortic aneurysms, peripheral vascular disease, cerebrovascular disease, cancer, trauma, and congenital malformations that may cause or display vascular manifestations, and the like.

Quantitative measures of a pathology can be obtained. For example, a quantity module which is part of the system can be used to measure the size of a blockage (e.g., a plaque). Based on such quantitative measures, the system will implement rules in the knowledge base for designing an interventional treatment device.

In yet another aspect, at least one knowledge base comprises clinical information related to a specific patient for which a device is being designed. This database can include such demographic information as age, sex, drug history, medical history, medical billing information, and the like. This portion of the system can be encrypted so that while information can be continually added to other knowledge bases (e.g., by remote system users), information within the patient-specific knowledge base cannot be tampered with. However, preferably, even information provided by remote system users will be stored in temporary data files until a system operator enables the system to accept the information. Information relating to populations of patients also can be stored for comparison with information relating to the specific patient.

In one aspect, the system implements a Finite Element Method (FEM) to perform numerical analysis of device parameters. Commercial FEM packages such as ANSYS or ABAQUS can be used. Typical FEM software comprises modules to create an element mesh from a plurality of device segments (e.g., to create a representation of a simulated device), to analyze a defined problem, and to review results of modified parameters on device design. Output can be displayed and/or printed.

FEM breaks down the simulated device's structure into simple segments such as blocks comprising nodes. Elements such as shells, solids, bricks, or beams also can be used. The behavior of an individual element is described mathematically, and sets of equations representing an entire device are then joined together to form a mesh, connecting at nodes or shared lines. Parameters such as deformation forces and torques, temperature distributions that causes thermal expansion and stress, can be applied directly to nodes or to elements with appropriate commands (e.g., by selecting selectable options displayed on the interface of the user device or by inputting variables into a displayed command line). For instance, flexibility of a segment corresponding to the tip of a simulated catheter can be tested with an embedded FEM engine, over a range of different materials. Additionally, the engine can be used to provide a quantitative measure representing the interaction between a catheter and another device such as guidewire Based on available information from analysis of volume images of a patient's body cavity or lumen, clinical input, and the user's selection of geometry, materials, and other design parameters for the simulated device, the system reports intermediate results (e.g., proposed simulations) to the user that eventually led to proposed solutions and confidence measures (e.g., simulations of devices which are predicted to be able to navigate and function optimally in the body cavity or lumen of the specific patient). Confidence measures represent the system's assessment of how good the proposed solutions are perceived to be based on rules contained within the knowledge base. When the user wants the system to justify a request for some information, he or she can ask why by inputting a query on the display of the user display which is part of the system (e.g., a PC which is connectable to the network). The system will derive a response from stored static information or will display and/or print the rules that the system is currently considering.

However, a user can overwrite one or more parameters selected by the system and can select his or her own variables. For example, based on a simulated vascular model displayed on the user's user interface, the user can select specific vessel locations (e.g., by pointing and clicking using a mouse) and can define a cross-sectional plane to section the model. A drawing sketch can then be created from the cross-section for free drafting of the tip shape of a simulated catheter with reference to the vascular model. The user can interactively modify the tip shape at this stage to obtain satisfactory result. This method creates planar curve shape based on the vasculature model. When a "new design" of the tip shape is generated, the basic parameters of the new design can be inputted into the system by the user to directly modify a simulated device or to provide facts to the shape knowledge base for consideration. The system can then recommend these parameters to create new simulations or to modify the existing simulation.

As discussed above, the expert system used to provide information to the knowledge bases of the system preferably comprises an inference engine which enables the system to manipulate input data from a user to arrive at one or more possible answers to a question by a user. Answers are derived using the rules and facts in the one or more knowledge bases. In a preferred embodiment, a goal-driven expert system is used to query the knowledge base. For example, in querying the device shape knowledge base, the main action performed by the system is to try to determine whether a particular device shape may be used based on the captured information relating to the patient's body cavity or lumen. Preferably, the inference engine of the expert system controls its searches based on information specific for the patient. For example, if a stent is intended to be used in the patient's brain, the system searches parameters relating to only very small stents.

Similarly, in querying the device materials knowledge base, the main action performed by the inference engine of the expert system is to try to determine whether particular device materials should be used based on the available information relating to interactions between the materials and particular body cavities or lumens (e.g., such as blood vessels).

In general, goal-driven searching is preferred because it is directed towards either confirming or rejecting a particular hypothesis, and it causes the reasoning displayed on the user interface to appear more focused and logical. This also builds the user's understanding and confidence in the system's actions. An example of a goal-driven search engine is the MYCIN project search engine, of Stanford University (see, e.g., Evans, et al., 1994, *Adv. Exp. Med. Biol.* 349: 87-96.

Modeling Simulated Devices by Segments

In one aspect of the invention, a simulated device is designed in segments which are then joined to form the device. Segments can be assembled lengthwise as well as in layers. Each segment can be designed in stages, by selecting geometry, material or functional parameters and design or information parameters for each segment. Modeling is parametric in the sense that it relies on data relating to design parameters of known devices or newly simulated devices which are stored in one or more knowledge bases of the system.

Generally, catheters can be modeled hierarchically in four segments, e.g., tip, hook, shaft and hub, each of which can be joined along the longitudinal axis of the device. The body of the catheter is generally straight over most of its length and may have a different configuration at the tip. In multilayered catheter designs, one tube is additionally stretched or extruded over another to form a bond. The materials used in each layer determine the overall performance characteristics of the catheter. Most multi-layered catheters consist of an inner layer of plastic over which a layer of filaments or wire is attached. This overlying "braiding" layer can comprise nylon, woven Dacron, stainless steel, and the like. Another layer of plastic typically is extruded over the inner layer and the braiding layer and is firmly bonded thereto to generate an external layer of the catheter.

The inner layer of the catheter generally provides a smooth surface through which guidewires, contrast agents, therapeutic drugs and devices can be passed. Properties of the overlying layer (e.g., thickness and/or density of braiding) determine such parameters as stiffness and torque control of the catheter. Thinner walls generally allow high flow characteristic but provide less torque control and strength. If thinner walls are desired, braiding can be incorporated into the inner layer and the overall number of layers of the device can be reduced. Use of a nylon layer or core can impart stiffness to a heat-resistant catheter.

Components of the external layer are also important determinants of catheter performance. For example, the external layer must be impregnated with a radioopaque material such as barium or bismuth to provide the catheter with radioopacity for easy fluoroscopic visualization. This process may soften the catheter material and may produce fine pitting of the surface of the catheter, leading to increased thrombogenicity. To compensate, radioopaque materials may be incorporated in the middle layers of the catheter, or a coating of silicon or non-thrombogenic material may be applied to the outer catheter surface.

A simulated segment's structure can be described in terms of its backbone geometry which can be defined by a sequence of rod points with a $G^1$ continuity constraint. The curvature or "central curve" of the backbone can be changed by interactive modification by a user during a design run or by deformation during a verification test (e.g., using the intervention simulation system as described below). The subdivision of the rods along the simulated device backbone coincides with the generation of finite elements by the FET engine of the simulation system.

The compound cross-section perpendicular to the central curve is defined by an explicit formula. It varies with multiple internal loops and single external close contours along the central curve. Therefore, a profile description of a simulated device may be expressed in terms of parameters relating to the central curve and a few other profile parameters that can vary independently. The surface geometry of a catheter is then constructed one piece or segment at a time, by sweeping the variable profile parameters along the smooth central curve. A simulated device can be reconstructed from a series of surfaces (e.g., 4-node elements) or bricks (e.g., 8-node elements) and then physical properties, such as stiffness, can be applied to individual elements. If a surface is not hollow and relatively thin, it can be modeled as beam elements containing two nodes.

Other interactive modifications also can be implemented such as mouse-controlled rubber-banding and rod modification as are known in the art.

Having selected a particular geometry or shape, parameters based on functional features of the simulated device are selected and/or modified, superimposing a layer of functional features on a representation of the geometry of a device previously selected. For example, this stage can include tip and/or hub design, providing injection ports or otherwise tapering the contours of the device to accommodate a portion of a patient's body cavity or lumen. An edge rounding technique with constant radius is used to construct a tip feature that may provide safe access to the blood walls. Because the flexibility of a catheter largely relies on corewire design and the material used, a sweeping operation can be used to describe a corewire incorporated into the device. This operation consists of combining circular motion and axial motion of a cross-sectional circle along a helical control curve. The helical control curve of the corewire is conjugated to the central curve of the simulated device.

Similarly, holes or ports can be simulated in the device by cutting cylindrical objects off the simulated device at user-specified points along the central curve and in given directions. For example, a catheter tip may have single or multiple side holes (e.g., through holes, blind or spiral styles). The presence of side holes allows for increased volume or rate of radioopaque dye injection and reduces the tendency for catheter recoil. Some catheter tip designs may, additionally or alternatively, incorporate a soft tip.

The hub of the catheter is bonded to the body and must have a strong and airtight seal. Specific design features include a female lock for syringe or manifold attachment, a squared or wing-like shape for easier handling, and imprinting of an identifier on the hub for easy identification. For example, a description of catheter length, diameter, softness, or other features can be imprinted on the hub. The internal portion of the hub must have a smooth taper to facilitate guidewire insertion. In many designs, shrink tubing or a sleeve to decrease the chance of kinking or bending, reinforces the hub connection to the body of the catheter.

Modifications in catheter design allow for the device to perform specialized functions such as stent and coil delivery, angioplasty and other interventional procedures. In one aspect, modifications in a device simulation represented on the display of a user device of the system are obtained by performing feature operations such as shape sweeping, extruding, holing, braiding, shelling, hub construction, and combinations thereof.

After desired functional attributes are incorporated into the simulated device, additional design or "information" parameters can be added. Relevant information relating to the operation of particular devices during procedures can be made part of the system's one or more knowledge bases. For example, the tendency of a particular catheter tip design to increase the chance of arterial injury during selective coronary catheterization can be included as data within the device materials database and the user can query the system to recommend a simulation with a low tendency to cause arterial injury. Additional information could include specific examples of pre-existing patient anatomical irregularities other than the primary lesion to be treated, e.g., such as sharp angulation of a vessel proximal to a lesion, or an abnormal but not pathological narrowing of a vessel.

Simulation-Based Design

In a preferred aspect of the invention, the system simulates a path which represents at least a portion of a patient's body cavity or lumen and determines fit between the geometry of the device (with or without functional and information attribute layers) and the geometry of the path. The system simulates the design of the device in stages; first providing a simulation based on optimal shape (e.g., using the device shape database), then optimal function, then optimal information parameters.

For example, in one aspect, the vascular anatomy of a specific patient is represented by the system using central lines and corresponding radii to indicate the lumens of blood vessels within the patient (e.g., such as blood vessels in the heart or brain). A virtual catheter is represented as a sequence of rod elements with variable material property. Preferably, the virtual catheter is superimposed on the representation of the vascular anatomy to simulate navigation of the catheter within a blood vessel lumen. The movements of the catheter can be simulated to model rotating, advancing, and/or retracting the catheter within a lumen of a blood vessel in real-time (e.g., using a mouse, joystick, toggle, or an intervention simulator as described further below).

During the navigation process, the simulated catheter will negotiate with the vessel wall to generate a numerical path that is formed by an FEM calculation implemented by the simulation system. The device simulator system will recommend or modify material properties of the virtual catheter based on this FEM analysis, using material properties stored within the device materials knowledge database, preferably in combination with knowledge in the vascular materials knowledge database. The user thus is able to change the material properties of the virtual catheter (or one or more segments of the catheter) in order to achieve an optimized solution (e.g., for optimal fit of the catheter within the path). When the navigation of a blood vessel by a virtual catheter is completed, the 3D numerical path obtained from the simulation can be used to build a new catheter. This method usually creates non-planar curved catheter designs.

In one aspect, the system displays a ranked set of simulated devices which fit into a path of a lumen represented by the system, and a user can select one or more of a plurality of selectable options displayed on the interface of the user device, to alter one or more device parameters. The system can then modify the simulated devices according to the one or more parameters selected and display one or more of a new ranked set of simulated devices. As described above, the system also can display the list of rules being used to identify one or more simulated devices as optimal.

During navigation of the virtual device, the device may need to be modified in an iterative way. Users are able to interactively change the material property and device shape of the devices in order to achieve an optimized solution through the user display interface of the system which presents selectable options, such as check buttons, drop-down menus, command lines, dialogue windows, and the like. Upon selecting one or more selectable options, one or more design parameters are changed, and a new device is simulated. Multiple medical devices can be modeled on each other. For example, virtual stents, balloons and stent-grafts, etc., can be modeled on top of a virtual catheter. Processes of virtual stenting, ballooning or stent-grafting can be simulated to obtain virtual device configurations that are compatible with a newly designed virtual catheter.

Figures 1, 8A:
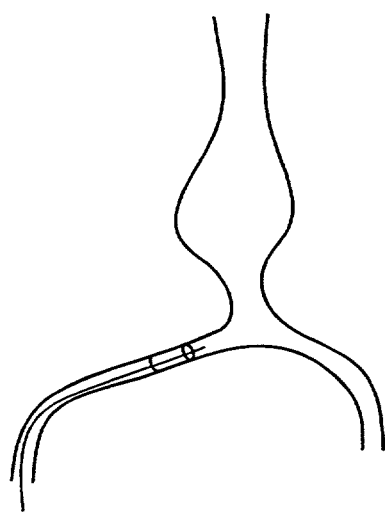
FIGS. 8A and B show simulation-based interventional device modeling according to one, aspect of the invention.
Figures 2, 8A:
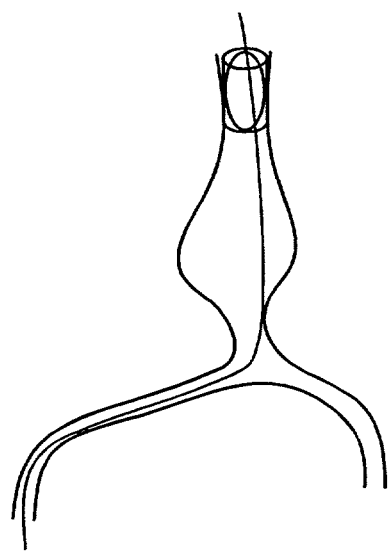
Figures 3, 8A:
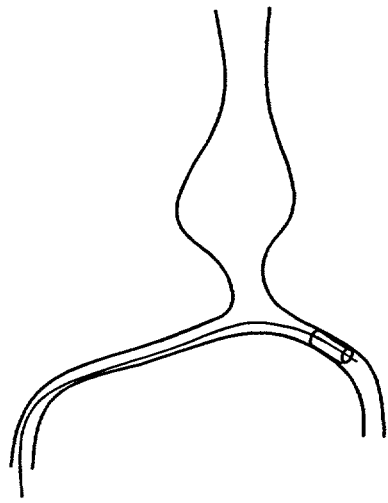
Figure 8B:
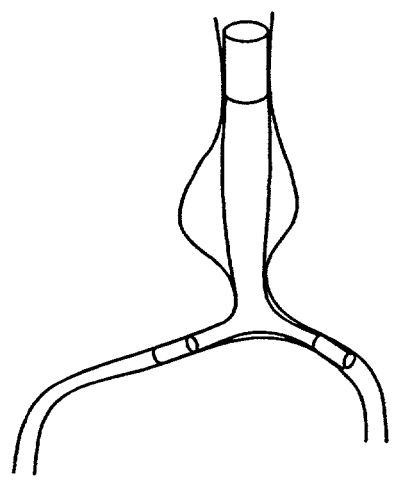
FIG. 8B shows an example of stent-graft design according to one aspect of the invention.
Figure 9:
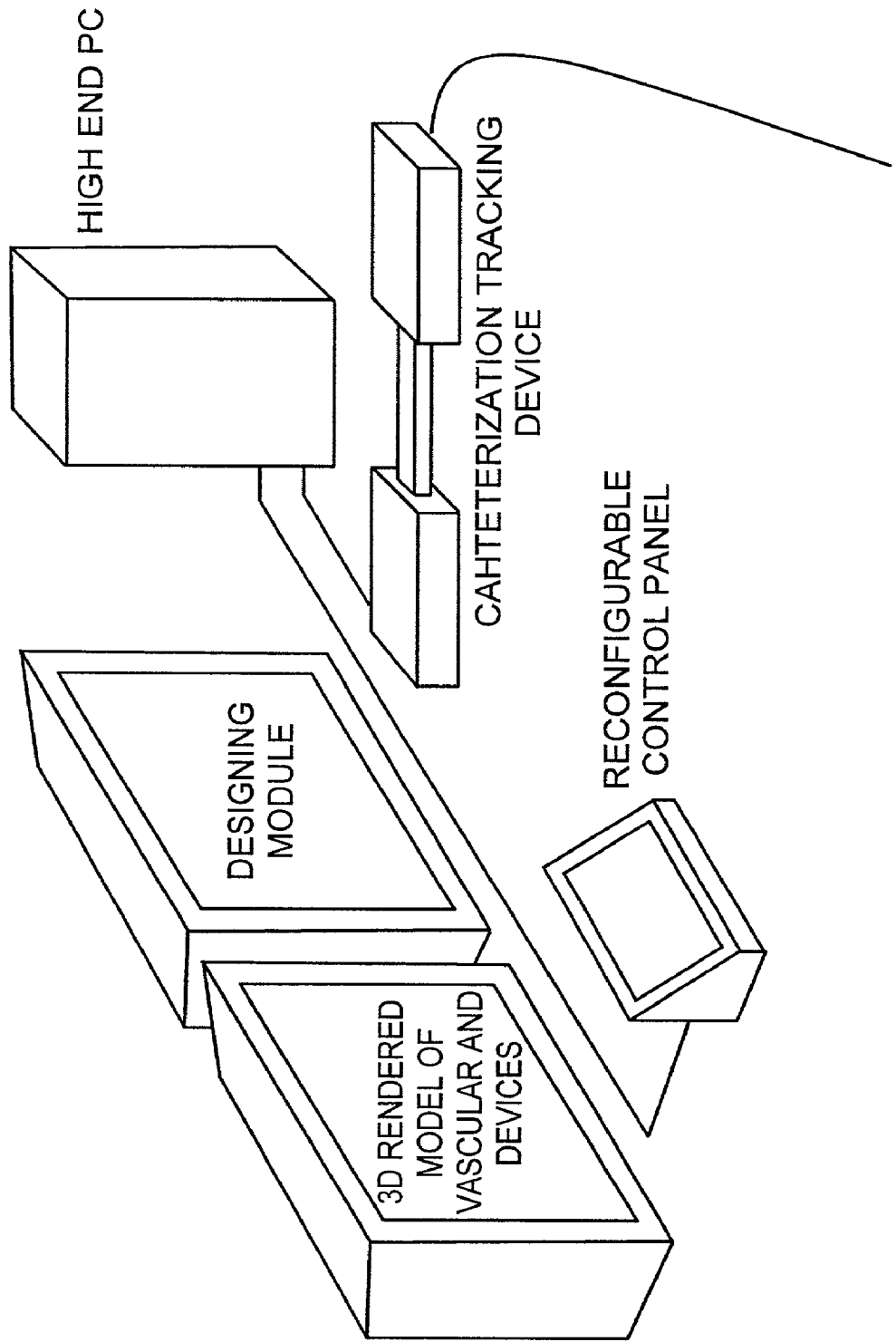
FIG. 9 illustrates a simulation system according to one aspect of the inventions.

FIGS. 8A and B illustrate an example how simulations can facilitate stent-graft design. As shown in the Figures, the deployment of multiple stents can be simulated (three are shown in FIG. 8B) to optimize stent deployment at a target region near a bifurcated blood vessel. With the information obtained from individual stents, a stent-graft can be modeled for further evaluation. This process of planning and evaluation can be refined iteratively, as illustrated in the flow chart shown in FIG. 2.

Intervention Simulation System

Variability encountered in normal patient vascular anatomy as well as in pathologies, often presents difficulty to physicians when choosing an interventional device for diagnostic or therapeutic procedures, such as catheterization. The invention further provides a simulation system for simulating the anatomy of a specific patient on which the device will be used. This can be realized by performing virtual device navigation inside a simulated body cavity or lumen using an incremental FEM engine. Such a simulation system is described in U.S. Provisional Application 60/273,733, filed Mar. 6, 2001, the entirety of which is incorporated by reference. The embedded FEM engine of the system is able to provide a real-time simulation of catheter/guide-wire interactions with blood vessels.

In one aspect, the intervention simulation system comprises a candidate medical device (e.g., designed by a User C, such as an engineer, as shown in FIG. 1) whose design is based on the optimal features identified by the simulation system described above. The candidate device generally comprises a first end for manipulation by a user and a portion comprising a second end which is insertable into a simulated body cavity or body lumen in a manikin. The manikin comprises an interface for receiving the portion comprising the second end and for interfacing with a simulated body cavity or lumen within the manikin. The interface also comprises a directional force feedback mechanism for exerting a directional force on the candidate medical device in response to a feedback signal received by the force feedback mechanism. This provides a user with a feeling that he/she is interacting with a real patient. Preferably, the directional force feedback mechanism provides resistance to forward motion but enables reverse motion in response to the feedback signal.

In one aspect, the directional force feedback mechanism comprises a rolling element (e.g., such as a shaft) coupled to the portion of the candidate device comprising the second end. An internal surface of the simulated cavity or lumen in the manikin in turn comprises an oblique slot for receiving the rolling element. In response to a feedback signal, forward movement of the second end causes the rolling element to be received by the slot, causing resistance to further forward motion. Preferably, a motor, such as a servo motor, controls movement of the rolling element. In a most preferred embodiment, the interface comprises both a directional force feedback mechanism and a tactile feedback mechanism. The tactile feedback mechanism provides continuous vibrational feedback to a user holding the candidate medical device. In one aspect, continuous vibrational feedback is provided through a continuously rotating motor in communication with the portion of the device comprising the second end. The tactile feedback mechanism simulates such parameters as blood flow, respiration, and the like.

The intervention simulator further provides a mechanism to continuously track a position of a least the second end of the medical device relative to the manikin. For example, the system can comprise one or more encoders for tracking translation and/or rotation of the device. In a currently preferred aspect, the system comprises a tracking unit which tracks the movement of the candidate medical device. The tracking system comprises a light source (e.g., a point light source), a signal processing circuit, and one or more optical sensors, and is placed within the interface in optical communication with the device and the simulated cavity or lumen through which the device is being navigated. The candidate device will reflect light to it from the light source and reflected light will be received by the optical sensor(s). Changes in reflected light picked up from the sensor(s) indicate movement of the candidate device as a result of manipulation.

In one aspect, two optical sensors are provided within the tracking unit, each perpendicular to the other.

In another aspect, the tracking unit is in the form of a rail along which the device can move. In a further aspect, the simulated device is looped around the tracking device and can be manipulated by pushing, pulling, and/or twisting. Tracking systems are further described in U.S. Provisional Application 60/273,733, filed Mar. 6, 2001. Preferably, tracking systems enable the intervention system to track the movement of two or more medical devices, for example, a catheter and guidewire, independently.

The intervention simulation system further comprises at least one first user device connectable to the network. The first user device comprises a first display interface for displaying a three-dimensional representation of a simulated body cavity or lumen of the specific patient for whom the candidate device is being designed. The first display interface also displays a three-dimensional representation of the simulated medical device corresponding to the candidate medical device which is interfaced with the manikin. Preferably, the system simulates the movement of the simulated device within the simulated body cavity or lumen in real-time when a first user manipulates the medical device interfaced with the manikin. In addition to simulating movement, the system can be used to simulate an operation of a medical device selected from the group consisting of: a surgical procedure, inflation or deflation of a balloon, injection of a radioopaque material into the body cavity or lumen, and the like.

To enhance the realism of the intervention simulation system, a simulated scanning display for displaying a two-dimensional image of the simulated body cavity or lumen is provided. The scanning display can be part of a scanning device such as an x-ray imaging system. Preferably, the scanning device and scanning display are coupled to a movable C-arm within scanning distance of the manikin. A re-configurable control panel (e.g., a touch screen) enables the first user to performing one or more of: image acquisition selection; image display; manipulating a table on which the manikin is placed; manipulating the position of a scanning device relative to th e manikin; and control of one or more shutter devices for limiting a field of view of a scanning device placed within scanning distance of the manikin.

The intervention simulation system and the device simulation system can interact, since components of both systems are connectable to the network. In one aspect, both systems are connectable to a database of patient images and/or medical data. This database may be part of one of the knowledge bases of the simulation system described above. Preferably, patient images include images of a body cavity or lumen from a patient affected by a pathology.

In response to intervention simulation, a user can again perform iterative modifications of the simulated device using the device simulation system. A knowledge base for storing data relating to interactions between a candidate device and the intervention simulation system also can be added to the system.

Variations, modifications, and other implementations of what is described herein will occur to those of ordinary skill in the art without departing from the spirit and scope of the invention. All of the references, patents, and applications identified above, are expressly incorporated herein in their entireties.

What is claimed is:

1. A method for designing a patient-specific medical device for accessing a body cavity or lumen of a patient comprising the steps of:
    providing a system that includes a device-shape knowledge base having facts and rules; the facts relating to geometries for each of at least one segment of one or more medical devices and the rules relating said geometries of each of the at least one segment of the one or more medical devices to geometries of at least a potion of a body cavity or lumen;
    providing data that relates to a three-dimensional geometric model of the patient's cavity or lumen to said system, the system performing an analysis using the provided data for determining correspondence between a geometry of the at least one segment of a specific one of the one or more medical devices and at least a portion of the three-dimensional geometric model; and
    (b) obtaining a recommendation from the system based on the analysis, the recommendation relating to the geometry of the patient-specific medical device for placement into the cavity or lumen.

2. The method according to claim 1, wherein the analysis uses the device shape knowledge bases to analyze the provided data.

3. The method according to claim 1, further comprising obtaining a volume image of the body cavity or lumen of the patient and generating the three-dimensional geometric model of the cavity or lumen from the volume image of the cavity or lumen.

4. The method according to claim 3, wherein the volume image is obtained from one or more of: an X-ray, Magnetic Resonance Imaging, Computer Tomography, rotational angiography, gadolinium enhanced MRA, and ultrasound.

5. The method according to claim 1, wherein the knowledge base comprises data relating to a physical property of the cavity or lumen.

6. The method according to claim 5, wherein the physical property is the elasticity of the cavity or lumen.

7. The method according to claim 1, further comprising displaying the recommendation on an interface of a user device connectable to a network.

8. The method according to claim 7, wherein the recommendation being displayed on the user device interface is in the form of a three-dimensional representation of the device.

9. The method according to claim 7, further comprising transmitting selectable options corresponding to design parameters of the device to the user device interface and displaying the selectable options thereon.

10. The method according to claim 9, wherein the selectable options are selected from the group consisting of: shape, material, flexibility, shape memory, stiffness, softness, pliability, stability, strength, contrast medium flow rate, length, size, and combinations thereof.

11. The method according to claim 9, further comprising selecting one or more of the selectable options and wherein the system simulates the design of the device based on the one or more selected options.

12. The method according to claim 7, wherein in response to a query, the system displays a rule used for making the recommendation.

13. The method according to claim 1, wherein the device is selected from the group consisting of a catheter, a guidewire, a balloon, a balloon-inflating device, a coil, a stent, stent-graft, an endoscope, a laparoscope, a bronchoscope, a surgical device, a vascular occlusion device, an optical probe, and a drug delivery device.

14. The method according to claim 1 or 13, wherein the design of more than one device is simulated.

15. The method according to claim 14, wherein parameters selected for one of the devices is based on parameters of at least one of the other devices.

16. The method according to claim 1, wherein the medical device is designed to access a lumen which is a blood vessel.

17. The method according to claim 1, wherein the device comprises multiple segments and wherein the method further includes selecting parameters of one or more of the multiple segments independently.

18. The method according to claim 17, wherein the device is selected from the group consisting of a catheter, a guidewire, a balloon, a balloon-inflating device, a coil, a stent, stent-graft, an endoscope, a laparoscope, a bronchoscope, a surgical device, a vascular occlusion device, an optical probe, and a drug delivery device.

19. The method according to claim 18, wherein at least one segment is selected from the group consisting of a tip, a rod element, a hook element and a hub.

20. The method according to claim 17, wherein at least two segments have varying material properties.

21. The method according to claim 1, wherein the system simulates a path representing at least a portion of the body cavity or lumen and wherein the method further comprises the system determining a best fit between the geometry of the device and the geometry of the path.

22. The method according to claim 1, wherein the method further comprises performing one or more feature operations to modify the recommended geometry.

23. The method according to claim 22, wherein the one or more feature operations are selected from the group consisting of shape sweeping, extruding, holing, braiding, edge rounding, and hub construction.

24. The method according to claim 1, further comprising performing a goal-driven search of the knowledge base to identify a device geometry which optimally corresponds to the model of the cavity or lumen.

25. The method according to claim 1, wherein the knowledge base includes clinical information relating to the patient.

26. The method according to claim 1, wherein the device geometry is determined using Finite Element Analysis.

27. The method according to claim 1, wherein the patient has a pathology affecting the structure of the body cavity or lumen.

28. The method of claim 1, further comprising:
generating a geometric model of the body cavity or lumen from the provided data; and
wherein said obtaining a recommendation from the system further includes obtaining a recommendation of a geometry, topology and physical properties of a device for placement into the cavity or lumen using the generated geometric model.

29. The method of claim 1, further comprising:
generating a geometric model of the body cavity or lumen from the provided data; and
wherein said obtaining a recommendation from the system further includes obtaining one or more recommendations of a geometry, topology and physical properties for one or more devices for placement into the cavity or lumen using the generated geometric model.

30. The method according to claim 1, wherein the facts relate to geometries for each of a plurality of segments of one or more medical devices and the rules relate said geometries of each of the plurality of segments of the one or more medical devices to geometries of at least a portion of a body cavity or lumen.

31. The method according to claim 1, wherein the facts relate to geometries for each of a plurality of segments of a plurality of medical devices and the rules relate said geometries of each of the plurality of segments of the plurality of medical devices to geometries of at least a portion of a body cavity or lumen.

32. A system for designing a medical device for accessing a body cavity or lumen of a patient, comprising:
a processor on which is executed a program, said program including:
a device shape knowledge base having:
a plurality of geometries for at least one segment of a device, rules for determining correspondence between a geometry of at least one segment and at least a portion of a model of the body cavity or lumen; and
an analysis section that analyzes data relating to a three-dimensional geometric model of a cavity or lumen of a patient using the device shaped knowledge base so as to output a recommendation relating to the geometry of the medical device for accessing the cavity or lumen.

33. The system according to claim 32, wherein the data is obtained from a plurality of scanned images of the cavity or lumen.

34. The system according to claim 33, wherein the system is in communication with a scanning device for obtaining the scanned images.

35. The system according to claim 32, wherein the system further comprises a user device comprising an interface for interfacing with a user which is connectable to the knowledge base and the network.

36. The system according to claim 35, wherein selectable options corresponding to design parameters of the device are transmitted to, and displayed on, the interface of the user device based on the data relating to the geometry of at least a portion of the cavity or lumen.

37. The system according to claim 36, wherein the selectable options are selected from one or more of the group consisting of: shape, material, flexibility, shape memory, stiffness, softness, pliability, stability, strength, contrast medium maximum flow rate, length, size.

38. The system according to claim 36, wherein when one or more of the selectable options are selected, the system simulates the design of the device based on the selected options.

39. The system according to claim 35, wherein the interface displays options for selecting one or more device parameters.

40. The system according to claim 35, wherein the interface comprises fields for inputting clinical data relating to the patient.

41. The system according to claim 35, wherein the knowledge base transmits data relating to the one or more device segment geometries to the user interface upon receiving data relating to the geometry of the cavity or lumen.

42. The system according to claim 41, wherein the data relating to the one or more device segment geometries is in the form of a graphical representation of the one or more device segments.

43. The system according to claim 35, wherein one or more feature operations are displayed on the interface and wherein selecting a feature operation modifies the shape of at least a segment of the device.

44. The system according to claim 43, wherein the one or more feature operations are selected from the group consisting of shape sweeping, extruding, holing, braiding, edge rounding, and hub construction.

45. The system according to claim 32, further comprising a device materials knowledge base comprising a plurality of data files relating to device materials and rules for determining suitability of a device material for at least one segment of the device.

46. The system according to claim 45, wherein the device materials knowledge base further comprises information relating to the elasticity of the portion of the body cavity or lumen.

47. The system according to claim 45, wherein the system simulates a path representing at least a portion of the body cavity or lumen and determines best fit between the geometry of the device and the geometry of the path.

48. The system according to claim 32, further comprising an expert system for identifying relationships between data in the knowledge base and data relating to the images.

49. The system according to claim 32, further comprising a data file comprising clinical information relating to the patient.

50. The system according to claim 32, further comprising a Finite Element Analysis engine.

51. A software suite for design of a medical device for accessing a body cavity or lumen, said software suite being stored on a computer readable medium and being configured for execution on a computer, said software suite comprising:
   a first component for storing a device shape knowledge base, the knowledge base comprising a plurality of geometries for at least one segment of the device and rules for determining correspondence between the geometry of the at least one segment and at least a portion of a geometric model of the body cavity or lumen, each rule comprising a statement with a certainty factor; and
   a second component comprising an executing function for executing one or more programs for determining whether one or more of the geometries of the at least one segment corresponds to the geometric model of at least a portion of the body cavity or lumen based on the rules for determining correspondence.

52. The software suite of claim 51, further comprising a second component for interfacing with a user device; wherein the second component provides a retrieval function for retrieving data relating to a geometric model of at least a portion of the body cavity or lumen and a transmitting function for transmitting the data to the knowledge base.

53. A method for designing a medical device for accessing a body cavity or lumen of a patient comprising:
   (A) providing data relating to a three-dimensional geometric model of the cavity or lumen to a system comprising a knowledge base which system performs an analysis using the provided data;
   (B) obtaining a recommendation from the system based on the analysis, the recommendation relating to the geometry of a device for placement into the cavity or lumen; wherein the knowledge base includes:
   (a) a diagnostic and pathological information knowledge base, where the provided data/information for the patient is inputted into the diagnostic and pathological information knowledge base,
   (b) a device shape knowledge base, and
   (c) a device physical material knowledge base;
   (C) analyzing the provided data and determining the physical properties of the body cavity or lumen of the patient; and
   wherein said obtaining a recommendation includes:
   (1) determining one or more appropriate shapes and designs of the device for placement in the body cavity/lumen using the determined physical properties of the body cavity or lumen of the patient and using facts and rules of the device shape knowledge base, and
   (2) determining one or more physical properties and/or characteristics of the device for placement in the body cavity/lumen using facts and rules of mechanics and physical properties of the body cavity/lumen being targeted of the device physical material knowledge base.

54. A method for designing a medical device for accessing a body cavity or lumen of a patient comprising:
   (A) providing data relating to a three-dimensional geometric model of the cavity or lumen to a system comprising a knowledge base which system performs an analysis using the provided data;
   (B) obtaining a recommendation from the system based on the analysis, the recommendation relating to the geometry of a device for placement into the cavity or lumen; and wherein the knowledge base includes:
   (a) a diagnostic and pathological information knowledge base, where the provided data/information for the patient is inputted into the patient specific diagnostic and pathological information knowledge base,
   (b) a device shape knowledge base; and
   (C) analyzing the provided data and determining the physical properties of the body cavity or lumen of the patient; and
   wherein said obtaining a recommendation includes determining the appropriate shape and design of the device for placement in the body cavity/lumen using the determined physical properties of the body cavity or lumen of the patient and using facts and rules of the device shape knowledge base.

55. A method for designing a medical device for accessing a body cavity or lumen of a patient comprising:
   (A) providing data relating to a three-dimensional geometric model of the cavity or lumen to a system comprising a knowledge base which system performs an analysis using the provided data;
   (B) obtaining a recommendation from the system based on the analysis, the recommendation relating to the geometry of a device for placement into the cavity or lumen;
   wherein the knowledge base includes:
   (a) a diagnostic and pathological information knowledge base, where the provided data/information for the patient is inputted into the patient specific diagnostic and pathological information knowledge base,
   (b) a device physical material knowledge base;
   (C) analyzing the provided data and determining the physical properties of the body cavity or lumen of the patient; and
   wherein said obtaining a recommendation includes determining physical properties and/or characteristics of the device for placement in the body cavity/lumen using facts and rules of mechanics and physical properties of the body cavity/lumen being targeted of the device physical material knowledge base.

56. The method of any one of claims 53-55, further comprising:
   generating a geometric model of the body cavity or lumen from the provided data; and
   wherein said determining includes determining the appropriate shape and design of the device for placement in the body cavity/lumen using the generated geometric model of the body cavity or lumen of the patient and using facts and rules of the device shape knowledge base.

57. An application program for execution on a processor, the software program being arranged so as to provide an output of one or more designs for a medical device that access a body cavity or lumen of a patient, said applications program including one or more knowledge bases and a processing part:

wherein said one or more knowledge bases includes:
(a) a diagnostic and pathological information knowledge base, where provided data/information for the patient is inputted into the diagnostic and pathological information knowledge base,
(b) a device shape knowledge base including facts and rules, and wherein the processing part includes instructions and criteria for:

analyzing the data/information being provided for the patient and determining the physical properties of the body cavity or lumen of the patient;

determining one or more appropriate shapes and designs of the device for placement in the body cavity/lumen using the determined physical properties of the body cavity or lumen of the patient and using the facts and rules of the device shape knowledge base, and providing an output of the determined one or more appropriate shapes and designs.

58. The application program of claim 57, wherein:
wherein said on or more knowledge bases includes:
(c) a device physical material knowledge base including facts and rules;

wherein the processing part includes instructions and criteria for:

determining one or more physical properties and/or characteristics of the device for placement in the body cavity/lumen using the facts and rules of mechanics and physical properties of the body cavity/lumen being targeted of the device physical material knowledge base; and wherein the instructions and criteria for providing an output further includes instructions and criteria for providing an output of the determined one or more physical properties and/or characteristics.

59. The application program of claim 58, wherein:
the device is comprised of a plurality of segments;
wherein the instructions and criteria for determining one or more physical properties and/or characteristics of the device for placement in the body cavity/lumen includes instructions and criteria for determining one or more physical properties and/or characteristics of each segment of the device using the facts and rules of mechanics and physical properties of the body cavity/lumen being targeted of the device physical material knowledge base.

60. The application program of claim 58, wherein the instructions and criteria of the processing part further includes instructions and criteria so as to create an inference engine for carrying out said determining one or more one or more physical properties and/or characteristics of the device.

61. The application program of any of claims 57-58, wherein:
the instructions and criteria for said analyzing the data/information being provided for the patient and determining the physical properties of the body cavity or lumen of the patient includes instructions and criteria for generating a geometric model of the body cavity or lumen from the provided data and wherein the instructions and criteria for determining one or more appropriate shapes and designs of the device for placement in the body cavity/lumen includes instructions and criteria for determining one or more appropriate shapes and designs of the device using the generated geometric model.

62. The application program of any of claim 57, wherein:
the device is comprised of a plurality of segments;
wherein the instructions and criteria for determining one or more appropriate shapes and designs of the device for placement in the body cavity/lumen includes instructions and criteria for determining one or more appropriate shapes and designs for each segment of the device.

63. The application program of any one of claims 57-58, wherein:
the device is comprised of a plurality of segments;
the instructions and criteria for said analyzing the data/information being provided for the patient and determining the physical properties of the body cavity or lumen of the patient includes instructions and criteria for generating a geometric model of the body cavity or lumen from the provided data and wherein the instructions and criteria for determining one or more appropriate shapes and designs of the device for placement in the body cavity/lumen includes instructions and criteria for determining one or more appropriate shapes and designs of each segment of the device using the generated geometric model.

64. The application program of claim 57, wherein the instructions and criteria of the processing part further includes instructions and criteria so as to create an inference engine for carrying out said determining one or more appropriate shapes and designs.

65. The application program of claim 57, wherein the instructions and criteria of the processing part further includes;
instructions and criteria for user overwriting of one or more parameters as automatically determined by the processing part; and
for causing the respective one or more of the knowledge bases to learn new parameters associated with a new design or physical property from such overwriting.

66. The application program of claim 57, wherein the processing part further includes instruction and criteria for:
emulating a device having one of the outputted determined one or more appropriate shapes and designs;
simulating navigation of at least a portion of the device from the entry point of a patient's body to the body cavity or lumen; and
determining changes to the design and proving an output of such changes based on said simulating and the facts and rules of the knowledge data bases.

* * * * *